(12) United States Patent
Asahina et al.

(10) Patent No.: US 12,295,609 B2
(45) Date of Patent: May 13, 2025

(54) ULTRASOUND TREATMENT TOOL

(71) Applicant: Olympus Medical Systems Corp., Tokyo (JP)

(72) Inventors: Marina Asahina, Sagamihara (JP); Tsubasa Niiyama, Hachioji (JP); Yoshitaka Fujii, Atsugi (JP); Motomu Nagata, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 17/885,278

(22) Filed: Aug. 10, 2022

(65) Prior Publication Data

US 2023/0051981 A1 Feb. 16, 2023

Related U.S. Application Data

(60) Provisional application No. 63/232,387, filed on Aug. 12, 2021.

(51) Int. Cl.
*A61B 17/32* (2006.01)
*A61B 17/00* (2006.01)

(52) U.S. Cl.
CPC ........... *A61B 17/320092* (2013.01); *A61B 2017/00367* (2013.01); *A61B 2017/320082* (2017.08); *A61B 2017/320095* (2017.08)

(58) Field of Classification Search
CPC .......... A61B 17/320092; A61B 2017/320082; A61B 2017/320095; A61B 2017/00367; A61B 17/320068
See application file for complete search history.

(56) References Cited

U.S. PATENT DOCUMENTS 5,989,264 A * 11/1999 Wright ............. A61B 17/22012
606/113
2006/0079874 A1* 4/2006 Faller ............. A61B 17/320092
606/40

(Continued)

FOREIGN PATENT DOCUMENTS

WO 2018/011896 A1 1/2018
WO WO-2020136888 A1 * 7/2020 ............. A61B 17/29

OTHER PUBLICATIONS

Espacenet translation of WO 2020136888 A1 (Year: 2020).*

*Primary Examiner* — Katherine H Schwiker
*Assistant Examiner* — Zehra Jaffri
(74) *Attorney, Agent, or Firm* — Morgan, Lewis & Bockius LLP

(57) ABSTRACT

An ultrasound treatment tool includes a handle 6, a vibration transmitting member 13 that is formed in an elongated shape, the vibration transmitting member being configured to transmit an ultrasound vibration generated by a vibration generation source, a holder 112 configured to hold the vibration transmitting portion 13, and a rotary knob 9 configured to rotate about a longitudinal axis Ax1 of the vibration transmitting portion 13 in accordance with a user operation. The holder 112 and the rotary knob 9 are integrally coupled with each other, and are positioned respectively in a radial direction about the longitudinal axis Ax1 with respect to the handle 6. One of the holder 112 and the rotary knob 9 is positioned in a direction along the longitudinal axis Ax1 with respect to the handle 6.

20 Claims, 20 Drawing Sheets

(56) References Cited

U.S. PATENT DOCUMENTS

| | | | |
|---|---|---|---|
| 2008/0171938 A1* | 7/2008 | Masuda | A61B 18/14 600/437 |
| 2012/0078249 A1* | 3/2012 | Eichmann | A61B 17/2841 606/45 |
| 2012/0116389 A1* | 5/2012 | Houser | A61B 17/320092 606/1 |
| 2014/0142573 A1* | 5/2014 | Masuda | A61B 18/1445 606/51 |
| 2016/0106456 A1* | 4/2016 | Xue | A61B 17/320092 606/169 |
| 2016/0302840 A1* | 10/2016 | Scheib | A61B 18/00 |
| 2019/0117246 A1* | 4/2019 | Tanaka | A61B 17/320092 |
| 2019/0142450 A1* | 5/2019 | Shimamura | A61B 17/320092 606/169 |
| 2020/0029997 A1 | 1/2020 | Shimamura et al. | |

\* cited by examiner

ULTRASOUND TREATMENT TOOL

RELATED APPLICATION DATA

This application is based on and claims priority under 35 U.S.C. § 119 to U.S. Provisional Application No. 63/232,387 filed on Aug. 12, 2021, the entire contents of which are incorporated herein by reference.

FIELD OF THE DISCLOSURE

The present disclosure relates to an ultrasound treatment tool.

BACKGROUND

Ultrasound treatment tools can apply an ultrasonic energy to a site subject to treatment (hereinafter, target site) in a living tissue (for example, Patent Literature 1).

An ultrasound treatment tool described in Patent Literature 1 includes a handle, a vibration transmitting member, a holder, and a rotary knob described below.

The handle is a portion grasped by an operator, such as surgeon.

The vibration transmitting member is formed in an elongated shape, and transmits ultrasound vibration generated by a vibration generation source.

The holder holds the vibration transmitting member.

The rotary knob rotates about a long axis of the vibration transmitting member according to a user operation. The rotary knob and the holder are connected to each other by using, for example, a pin or the like so as to move along with the rotation about the long axis. That is, the rotary knob rotates the holder and the vibration transmitting member according to the user operation.

Patent Literature 1: International Publication No. 2018/011896.

BRIEF SUMMARY OF EMBODIMENTS

An ultrasound treatment tool includes a handle. A vibration transmitting member is formed in an elongated shape and transmits an ultrasonic vibration generated by a vibration generating source.

A holder holds the vibration transmitting member. A rotary knob is configured to rotate about a longitudinal axis of the vibration transmitting member in response to a user operation.

The holder and the rotary knob are integrally coupled with each other. Both the holder and the rotary knob are positioned radially relative to the longitudinal axis. A location along the longitudinal axis of at least one of the holder and the rotary knob is fixed.

DETAILED DESCRIPTION

Hereinafter, modes (hereinafter, embodiments) to implement the present disclosure will be explained with reference to the drawings. The embodiments explained below are not intended to limit the present disclosure.

Moreover, like reference symbols are assigned to like parts in the description of the drawings.

Schematic Configuration of Treatment System

Figure 1:
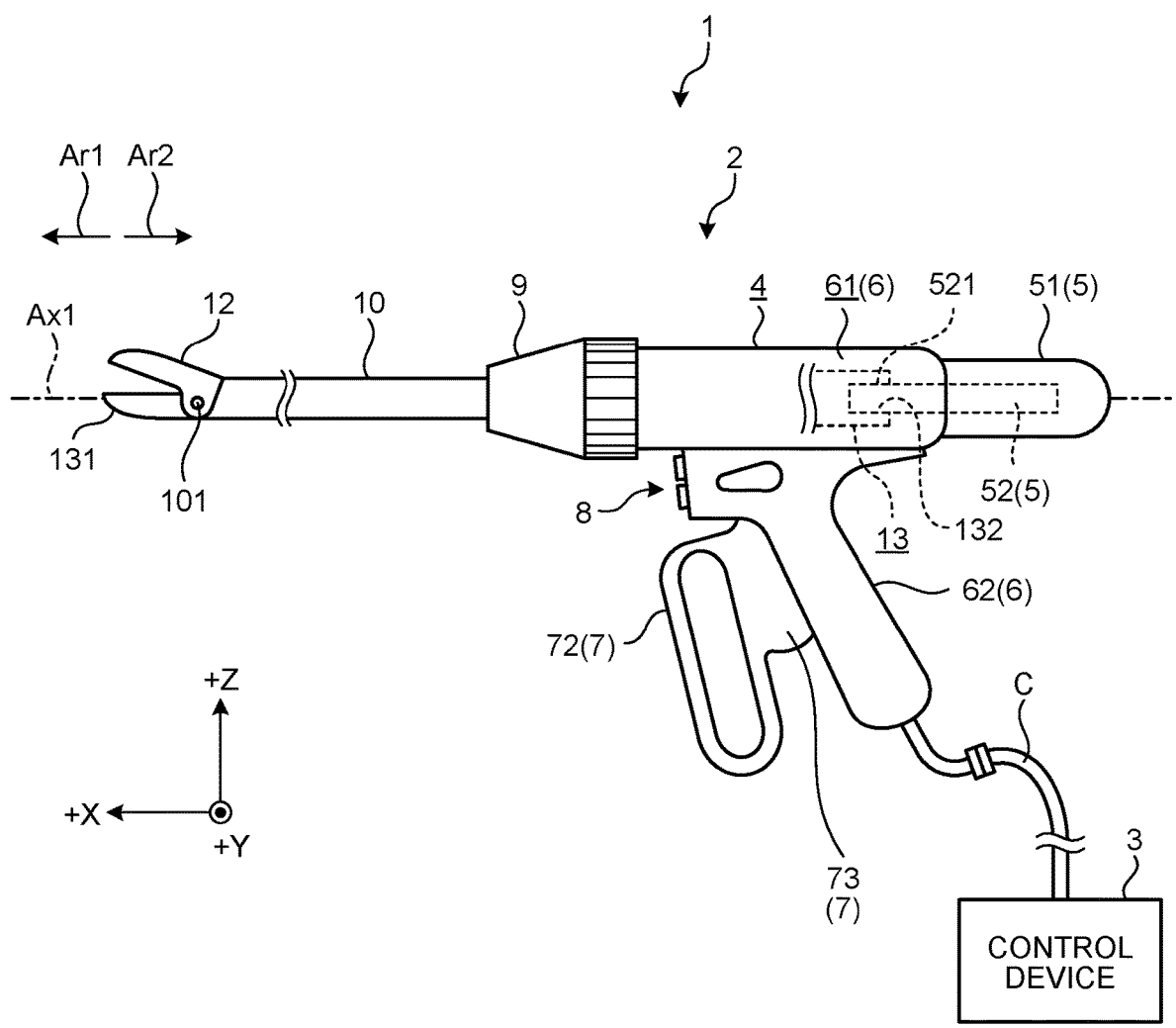
FIG. 1 is a diagram illustrating a treatment system according to an embodiment.

FIG. 1 is a diagram illustrating a treatment system 1 according to an embodiment.

The treatment system 1 applies a treatment energy to a site subject to treatment (hereinafter, target site) in a living tissue, and thereby treats the target site. The treatment energy in the present embodiment is an ultrasonic energy and a high frequency energy. Moreover, examples of the treatment that can be performed by the treatment system 1 according to the present embodiment include coagulation (sealing) of a target site, incision of a target site, or the like. The coagulation and the incision may be performed at the same time. This treatment system 1 includes, as illustrated in FIG. 1, an ultrasound treatment tool 2 and a control device 3. Hereinafter, the ultrasound treatment tool 2 is denoted as treatment tool 2 for convenience of explanation.

Configuration of Treatment Tool

In the following, for explaining the configuration of the treatment tool 2, XYZ coordinate axes of an X axis, a Y axis, and a Z axis perpendicular to one another are used. The X axis is an axis parallel to a center axis Ax1 (FIG. 1) of a shaft 10. The center axis Ax1 corresponds to a longitudinal axis according to the present disclosure. The Y axis is an axis perpendicular to a sheet surface of FIG. 1. The Z axis is an axis along a top-bottom direction of FIG. 1. Moreover, in the following, one side (+X axis side) along the center axis Ax is denoted as a distal end side Ar1, and the other side (−X axis side) is denoted as a proximal end side Ar2.

Figure 2:
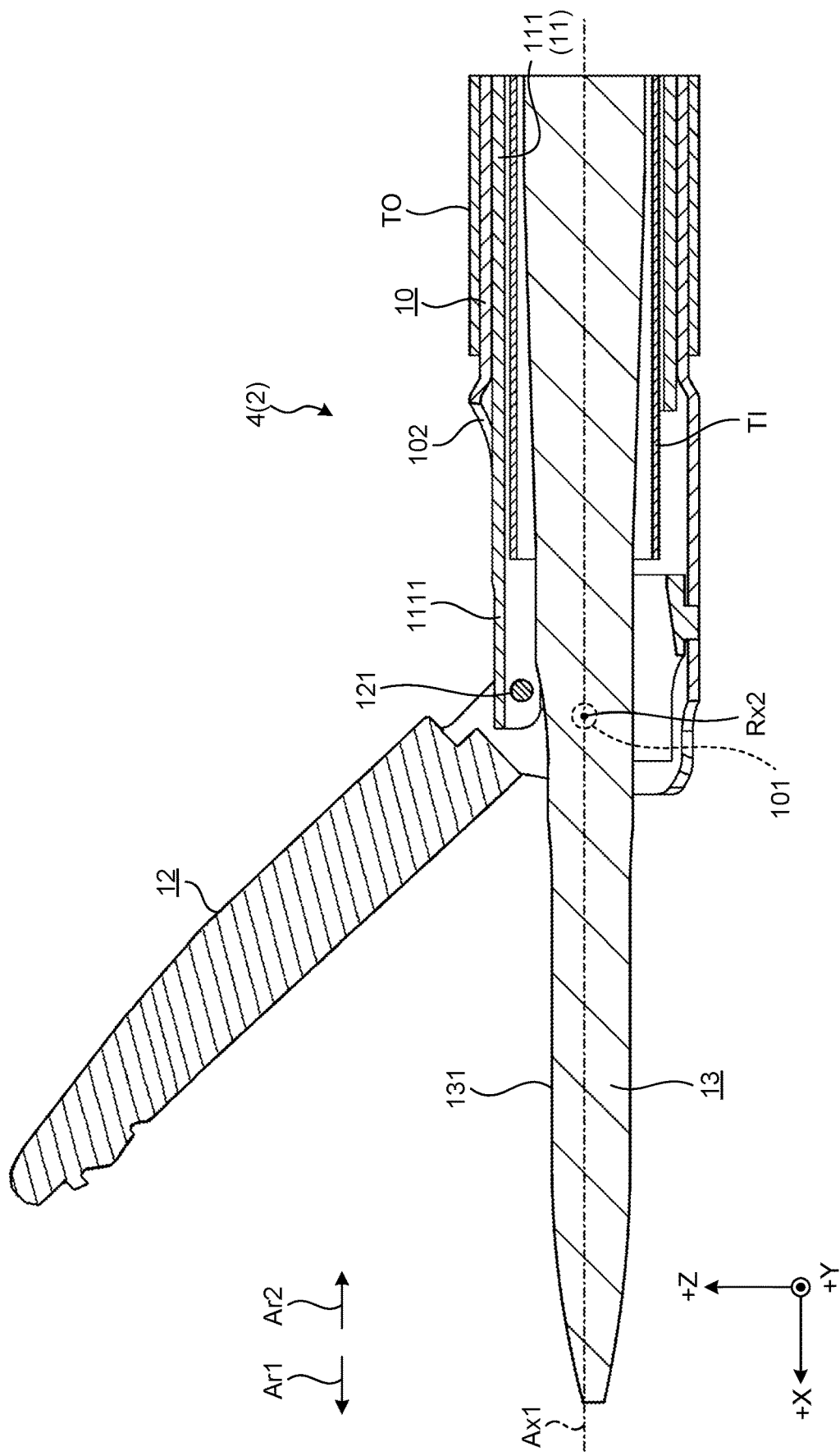
FIG. 2 is a diagram explaining a configuration of a treatment tool.
Figure 3:
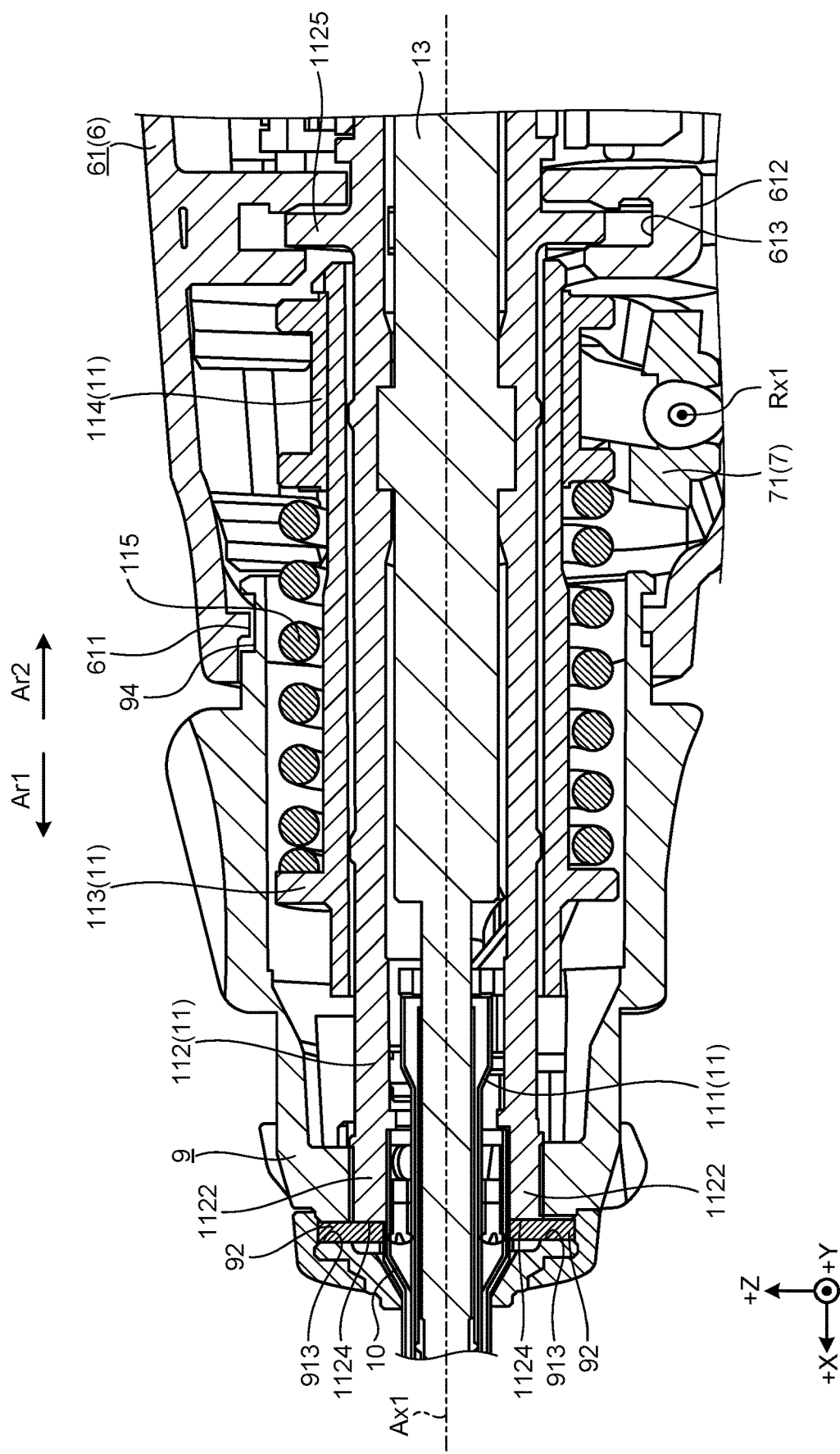
FIG. 3 is a diagram explaining the configuration of the treatment tool.

FIG. 2 and FIG. 3 are diagrams explaining the configuration of the treatment tool 2. Specifically, FIG. 2 and FIG. 3 are cross-section of the treatment tool 2 cut along an XZ plane including the center axis Ax1, and viewed from a +Y axis side (front side of the sheet of FIG. 1).

The treatment tool 2 is an ultrasound treatment tool that applies an ultrasonic energy and a high frequency energy to a target site, and that thereby treats the target site. This treatment tool 2 includes a handpiece 4 and an ultrasound transducer 5 (FIG. 1) as illustrated in FIG. 1 to FIG. 3.

The handpiece 4 includes a fixed handle 6 (FIG. 1, FIG. 3), a movable handle 7 (FIG. 1, FIG. 3), a switch 8 (FIG. 1), a rotary knob 9 (FIG. 1, FIG. 3), a shaft 10, an opening closing mechanism 11 (FIG. 2, FIG. 3), a jaw 12 (FIG. 1, FIG. 2), and a vibration transmitting member 13 as illustrated in FIG. 1 to FIG. 3.

The fixed handle 6 corresponds to a handle according to the present disclosure. The fixed handle 6 supports the entire treatment tool 2. This fixed handle 6 includes a substantially cylindrical casing body 61 that is coaxial with the center axis Ax1, and a handle main body 62 that extends toward a −Z axis side (lower side in FIG. 1) from the casing body 61, and that is grasped by an operator, such as a surgeon as illustrated in FIG. 1 or FIG. 3.

The movable handle 7 respectively accepts a closing operation and an opening operation that are user operations performed by the operator, such as surgeon. This movable handle 7 includes a handle base portion 71 (FIG. 3), an operating portion 72 (FIG. 1), and a connecting portion 73 (FIG. 1) as illustrated in FIG. 1 or FIG. 3.

The handle base portion 71 is positioned inside the fixed handle 6. A portion of the handle base portion 71 on a +Z axis side is axially supported in a rotatable manner about a first rotation axis Rx1 (FIG. 3) that is parallel to the Y axis, with respect to the fixed handle 6. Moreover, an end portion of the handle base portion 71 on the +Z axis side protrudes toward the +Z axis side in a branched state into two, and functions as an engaging portion (not illustrated) that engages with a slider 114 constituting the opening closing mechanism 11.

The operating portion 72 is a part that respectively accepts a closing operation and an opening operation performed by the operator, such as surgeon, and is positioned outside the fixed handle 6 as illustrated in FIG. 1.

The connecting portion 73 is arranged astride the inside and the outside of the fixed handle 6, and is a part to connect the handle base portion 71 and the operating portion 72.

The movable handle 7 rotates in a counterclockwise direction in FIG. 3 about the first rotating axis Rx1 when the closing operation performed by the operator, such as surgeon, is accepted. That is, the operating portion 72 moves in a direction approaching the handle main body 62. On the other hand, the movable handle 7 rotates in a clockwise direction in FIG. 3 about the first rotating axis Rx1 when the opening operation performed by the operator, such as surgeon, is accepted. That is, the operating portion 72 moves in a direction separating from the handle main body 62.

The switch 8 is arranged to be exposed to the outside from a side surface of the handle main body 62 on the distal end side Ar1 as illustrated in FIG. 1 or FIG. 3. The switch 8 accepts a treatment operation performed by the operator, such as surgeon. The treatment operation is an operation to apply a treatment energy to a target site.

The rotary knob 9 has a substantially cylindrical shape coaxial with the center axis Ax1, and is arranged at the distal end side Ar1 of the casing body 61 as illustrated in FIG. 3. The rotary knob 9 accepts a rotation operation that is a user operation performed by the operator, such as surgeon. By the rotation operation, the rotary knob 9 rotates about the center axis Ax1 with respect to the casing body 61. Furthermore, by the rotation of the rotary knob 9, the jaw 12 and the vibration transmitting member 13 rotate about the center axis Ax1.

An attachment mechanism of the rotary knob 9 to the casing body 61 will be explained in "About Attachment mechanism of Rotary knob and Holder to Casing Body" described later.

The shaft 10 is a cylindrical pipe constituted of an electrically conductive material, such as metal, and corresponds to a cylindrical pipe according to the present disclosure. This electrically conductive material corresponds to a first conductive material according to the present disclosure.

Moreover, in the shaft 10, a first pin 101 (FIG. 1, FIG. 2) that extends in a direction perpendicular to the sheet surface of FIG. 1, and that axially supports the jaw 12 in a rotatable manner about a second rotation axis Rx2 (FIG. 2) is fixed at an end portion on the distal end side Ar1.

Furthermore, in the shaft 10, a notch portion 102 (FIG. 2) that extends toward the proximal end side Ar2 from the distal end is arranged on the +Z axis side of an end portion on the distal end side Ar1.

An outer peripheral surface of the shaft 10 explained above is covered with an outer tube TO having electrical insulation (FIG. 2).

The opening closing mechanism 11 is a mechanism that opens and closes the jaw 12 with respect to an end portion 131 (hereinafter, denoted as treating portion 131) of the vibration transmitting member 13 on the distal end side Ar1 in response to the opening operation or the closing operation performed by the operator, such as surgeon, to the movable handle 7. The treating portion 131 corresponds to a blade according to the present disclosure. This opening closing mechanism 11 includes an inner pipe 111, a holder 112 (FIG. 3), a slider rest 113 (FIG. 3), and a slider 114 (FIG. 3) as illustrated in FIG. 2 or FIG. 3.

the inner pipe 111 is a cylindrical pipe having a diameter smaller than the shaft 10, and is inserted into the inside of the shaft 10 coaxially with the shaft 10.

In this inner pipe 111, an arm portion 1111 that protrudes toward the distal end side Ar1 is arranged on the +Z axis side of the end portion of the distal end side Ar1 as illustrated in FIG. 2. To this arm portion 1111, a second pin 121 that is arranged in the jaw 12 and that extends parallel to the second rotation axis Rx2 (the first pin 101) is inserted.

The holder 112 is constituted of a material having an electrical insulating material, such as resin, and has a substantially cylindrical shape. The holder 112 holds the vibration transmitting member 13 in a state in which the vibration transmitting member 13 is inserted thereinside. This holder 112 is inserted in the inside of the rotary knob 9 and the casing body 61 astride the rotary knob 9 and the casing body 61 as illustrated in FIG. 3.

The holder 112 is attached to the casing body 61 in a state in which rotation about the center axis Ax1 with respect to the casing body 61 is allowed and movement along the center axis Ax1 is restricted. Moreover, an end portion of the holder 112 on the distal end side Ar1 is attached to the rotary knob 9 in a state in which rotation about the center axis Ax1 with respect to the rotary knob 9 and movement along the center axis Ax1 are restricted.

An attachment mechanism of the holder 112 with respect to the casing body 61 will be explained in "About Attachment Mechanism of Rotary knob and Holder With Respect to Casing Body" described later. Moreover, a connection relationship between the rotary knob 9 and the holder 112 will be explained in "About Connection Relationship Among Rotary knob, Holder, and Slider Rest" described later.

Furthermore, an end portion of the shaft 10 on the proximal end side Ar2 is fixed to the holder 112, inserted into the inside of the end portion of the holder 112 on the distal end side Ar1 as illustrated in FIG. 3.

The holder 112, the shaft 10, the jaw 12, and the vibration transmitting member 13 rotate about the center axis Ax1 together with the rotary knob 9, according to a rotation operation performed by the operator, such as surgeon, to the rotary knob 9.

The slider rest 113 is constituted of a material having an electrical insulation, such as resin, and has a substantially cylindrical shape. The slider rest 113 is arranged movably along the center axis Ax1 with respect to the holder 112 in a state in which the holder 112 is inserted thereinside.

An end portion of the slider rest 113 on the distal end side Ar1 is connected to the holder 112 in a state in which in movement along the center axis Ax1 with respect to the holder 112 is allowed and rotation about the center axis Ax1 is restricted.

A connection relationship of the holder 112 and the slider rest 113 will be explained in "About Connection Relationship among Rotary knob, Holder, and Slider Rest" described later.

Moreover, the end portion of the slider rest 113 on the distal end side Ar1 is connected to the rotary knob 9 in a state in which in movement along the center axis Ax1 with respect to the rotary knob 9 is allowed and rotation about the center axis Ax1 is restricted.

A connection relationship of the rotary knob 9 and the slider rest 113 will be explained in "About Connection Relationship among Rotary knob, Holder, and Slider Rest" described later.

Furthermore, an end portion of the inner pipe 111 on the proximal end side Ar2 is fixed to the end portion of the slider rest 113 on the distal end side Ar1, inserted into the inside of the holder 112 as illustrated in FIG. 3.

The slider rest 113 and the inner pipe 111 rotate about the center axis Ax1 together with the rotary knob 9 according to a rotation operation performed by the operator, such as surgeon, to the rotary knob 9.

The slider 114 has a substantially cylindrical shape, and is arranged movably along the center axis Ax1 with respect to the slider rest 113 in a state in which the slider rest 113 is inserted thereinside. The slider 114 is engaged with an engaging portion (not illustrated) in the movable handle 7 as described above.

The opening closing mechanism 11 operates as described in the following, in accordance with an operation performed by the operator, such as surgeon, to the movable handle 7.

The slider 114 is pushed toward the distal end side Ar1 along the center axis Ax1 by the engaging portion (not illustrated) of the movable handle 7 according to the closing operation to the movable handle 7 by the operator, such as surgeon. Moreover, the slider rest 113 receives a pushing force toward the distal end side Ar1 from the slider 114 through a coil spring 115 (FIG. 3) arranged between itself and the slider 114. Furthermore, the inner pipe 111 moves to the distal end side Ar1 along the center axis Ax1 together with the slider rest 113. Moreover, the arm portion 1111 pushes the second pin 121 toward the distal end side Ar1. The jaw 12 rotates in a counterclockwise direction about the second rotation axis Rx2 in FIG. 2. At this time, because the second pin 121 moves about the second rotation axis Rx2, maintaining a certain distance, the arm portion 1111 moves to the distal end side Ar1 while deforming toward the +Z axis side on which the notch portion 102 is arranged. That is, the jaw 12 moves in a direction approaching the treating portion 131 (closing direction).

Moreover, the jaw 12 rotates in a clockwise direction about the second rotation axis Rx2 in FIG. 2 according to the opening operation to the movable handle 7 by the operator, such as surgeon. That is, the jaw 12 moves in a direction separating from the treating portion 131 (opening direction).

As described, the jaw 12 opens and closes with respect to the treating portion 131 according to an operation performed by the operator, such as surgeon, to the movable handle 7, and thereby grasps a target site between itself and the treating portion 131.

The coil spring 115 is used to make the grasping force to grasp the target site between the jaw 12 and the treating portion 131 uniform.

At least a part of the jaw 12 is constituted of an electrically conductive material. This electrically conductive material corresponds to a second conductive material according to the present disclosure.

The vibration transmitting member 13 is constituted of an electrically conductive material, and has an elongated shape linearly extending along the center axis Ax1. Moreover, the vibration transmitting member 13 is inserted into the inside of the inner pipe 111 in a state in which the treating portion 131 protrudes out to the outside as illustrated in FIG. 2. In this state, an end portion of the vibration transmitting member 13 on the proximal end side Ar2 is mechanically connected to an ultrasound vibrator 52 constituting the ultrasound transducer 5 as illustrated in FIG. 1. Specifically, the vibration transmitting member 13 and the ultrasound vibrator 52 are connected to each other as an external thread 521 arranged at an end portion of the ultrasound vibrator 52 on the distal end side Ar1 is screwed into an internal thread 132 arranged at the end portion of the vibration transmitting member 13 on the proximal end side Ar2. The external thread 521 corresponds to a first screw according to the present disclosure. Moreover, the internal thread 132 corresponds to a second screw according to the present disclosure. Although the internal thread 132 is arranged in the vibration transmitting member 13 and the external thread 521 is arranged in the ultrasound vibrator 52, not limited thereto, an external thread part may be arranged in the vibration transmitting member 13, and an internal thread part may be arranged in the ultrasound vibrator 52 inversely.

The vibration transmitting member 13 transmits the ultrasound vibration generated by the ultrasound transducer 5 from the end portion on the proximal end side Ar2 to the treating portion 131. In the first embodiment, the ultrasound vibration is axial vibration vibrating in a direction along the center axis Ax1.

An outer peripheral surface of the vibration transmitting member 13 is covered with an inner tube TI (FIG. 2) having electrical insulation, to ensure the electrical insulation between the shaft 10 and the inner pipe 111, and the vibration transmitting member 13.

The ultrasound transducer 5 corresponds to a vibration generation source according to the present disclosure. This ultrasound transducer 5 includes a transducer (TD) case 51 and the ultrasound vibrator 52 as illustrated in FIG. 1.

The TD case 51 supports the ultrasound vibrator 52, and is detachably connected to the casing body 61.

The ultrasound vibrator 52 generates ultrasound vibrations under control of the control device 3. In the first embodiment, the ultrasound vibrator 52 is constituted of a bolt-clamped Langevin transducer (BLT).

Configuration of Control Device

The control device 3 overall controls operations of the treatment tool 2 through an electrical cable C (FIG. 1).

Specifically, the control device 3 detects a treatment operation performed by the operator, such as surgeon, to the switch 8 through the electrical cable C. When the treatment operation is detected, the control device 3 applies a treatment energy to a target site grasped between the jaw 12 and the treating portion 131 through the electrical cable C. That is, the control device 3 treats the target site.

For example, to apply an ultrasonic energy to a target site, the control device 3 supplies a driving power to the ultrasound vibrator 52 through the electrical cable C. Thus, the ultrasound vibrator 52 generates an axial vibration (ultrasound vibration) vibrating in a direction along the center axis Ax1. Moreover, the treating portion 131 vibrates at a desired amplitude by the axial vibration. To the target site grasped between the jaw and the treating portion 131, ultrasound vibration is applied from the treating portion 131. In other words, the ultrasonic energy is applied to the target site from the treating portion 131.

Moreover, for example, when a high frequency energy is applied to a target site, the control device 3 supplies a high frequency power to a portion between the jaw 12 and the vibration transmitting member 13 through the electrical cable C.

Specifically, the electrical cable C is electrically connected to the vibration transmitting member 13 through a first electrical pathway (not illustrated) arranged inside the fixed handle 6. Moreover, the electrical cable C is electrically connected to an electrically communication path P1 (refer to FIG. 4) through a second electrical pathway (not illustrated) arranged inside the fixed handle 6. This electrically communication path P1 is constituted of an electrically conductive material, and extends from the end portion on the proximal end side Ar2 to an end portion on the distal end side Ar1 on an outer peripheral surface of the holder 112. Furthermore, an end portion on the proximal end side Ar2 in the electrically communication path P2 is electrically connected to the second electrical pathway described above. On the other hand, an end portion on the distal end side Ar1 in the electrically communication path P1 is electrically connected to an end portion of the shaft 10 on the proximal end side Ar2. That is, the second electrical pathway (not illustrated) is electrically connected to the jaw 12 through the electrically communication path P1 and the shaft 10.

When a high frequency power is supplied to the portion between the jaw 12 and the vibration transmitting member 13, a high frequency current flows through the target site grasped between the jaw 12 and the treating portion 131. In other words, a high frequency energy is applied to the target site.

[About Connection Relationship Among Rotary knob, Holder, and Slider Rest]

Next, a connection relationship between the rotary knob 9 and the holder 112, a connection relationship between the holder 112 and the slider rest 113, and a connection relationship between the rotary knob 9 and the slider rest 113 will be explained sequentially.

Figure 4:
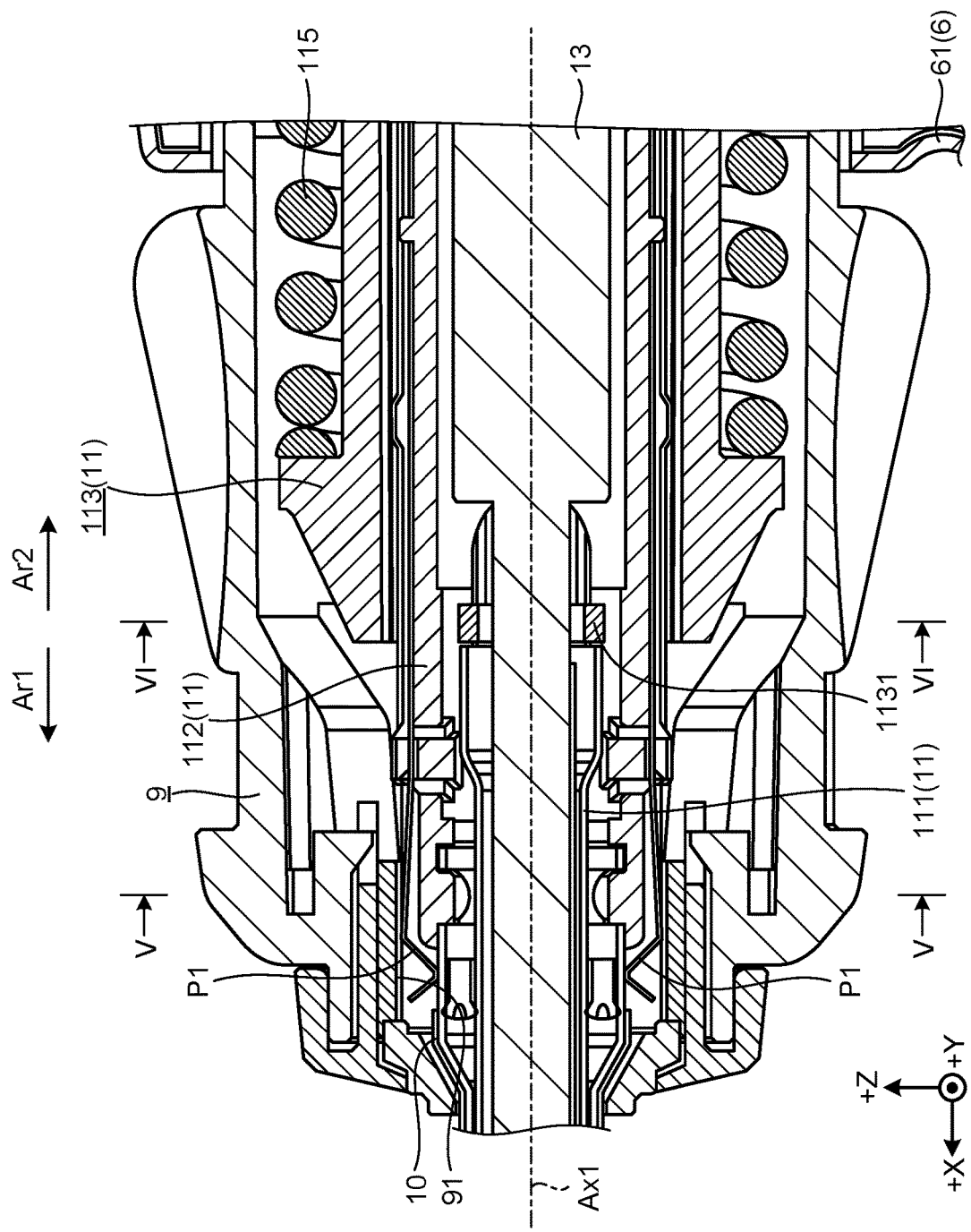
FIG. 4 is a diagram explaining a connection relationship of a rotary knob, a holder, and a slider rest.
Figure 5:
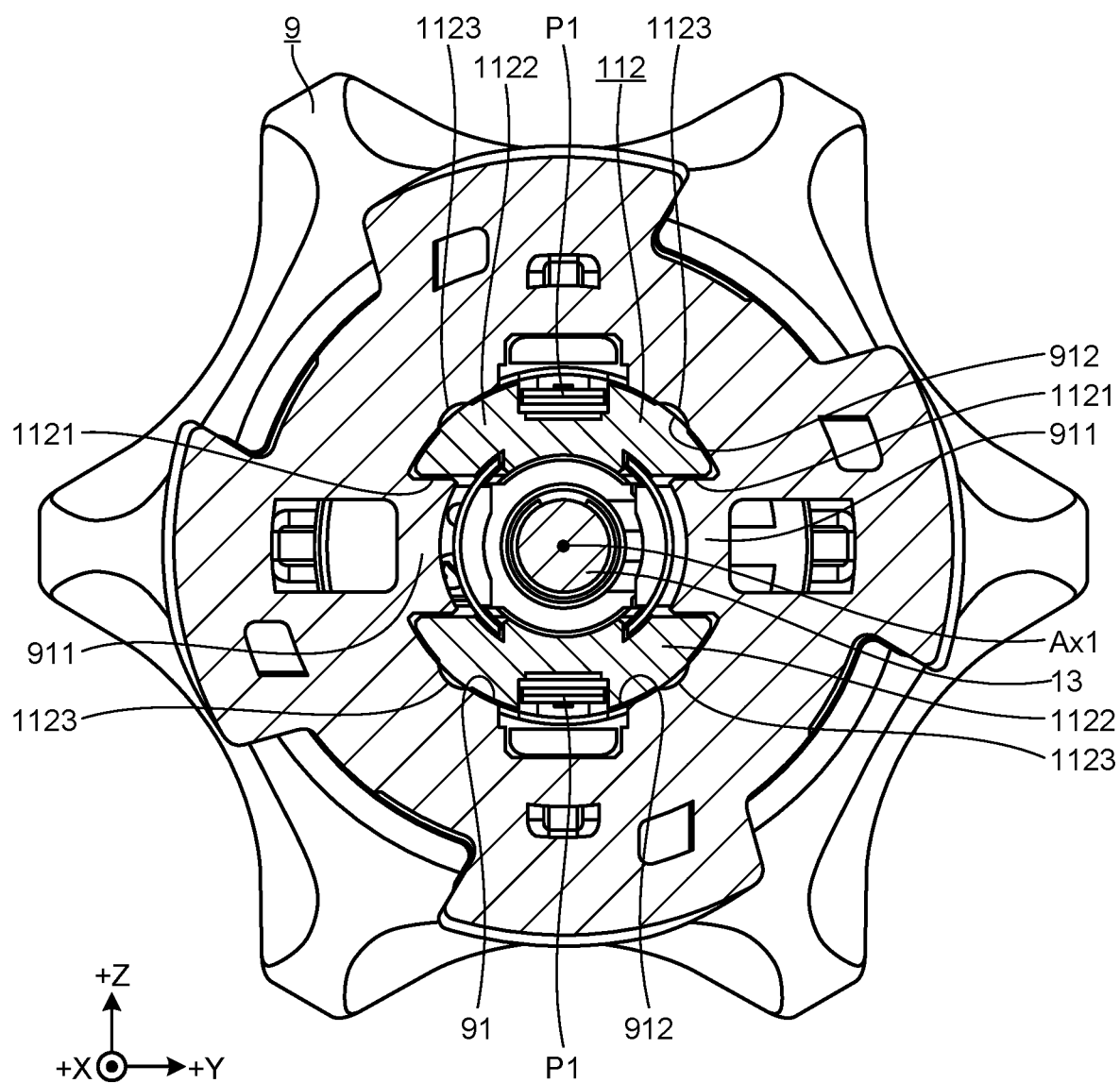
FIG. 5 is a diagram explaining a connection relationship of the rotary knob, the holder, and the slider rest.
Figure 6:
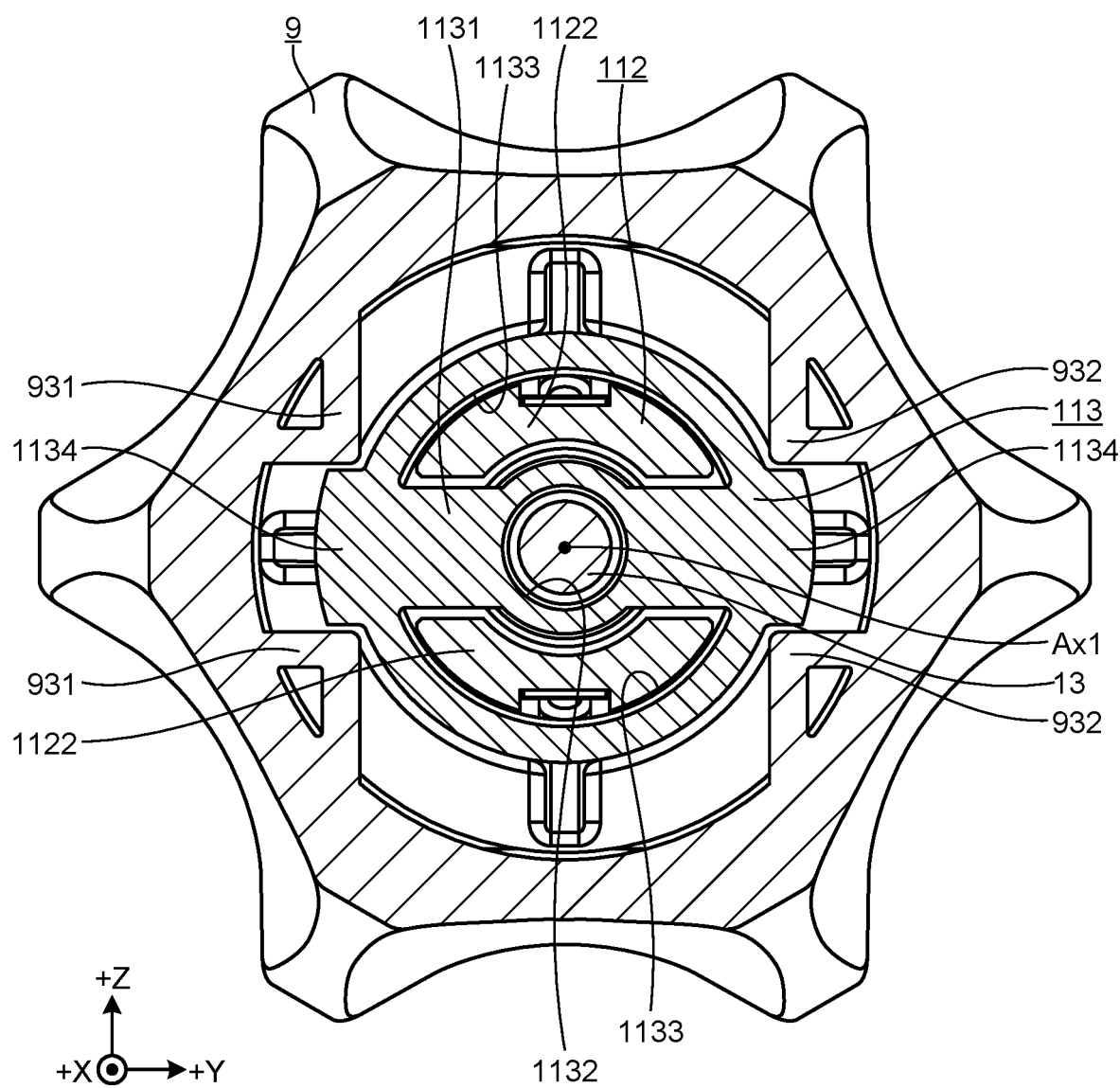
FIG. 6 is a diagram explaining a connection relationship of the rotary knob, the holder, and the slider rest.

FIG. 4 to FIG. 6 are diagrams explaining the connection relationship among the rotary knob 9, the holder 112, and the slider rest 113. Specifically, FIG. 4 is a cross-section corresponding to FIG. 3. FIG. 4 illustrates a state in which the rotary knob 9, the shaft 10, and the opening closing mechanism 11 rotate about the center axis Ax1 by a predetermined angle from a state illustrated in FIG. 3. FIG. 5 is a cross-section of the treatment tool 2 taken at a position of a line V-V illustrated in FIG. 4. FIG. 6 is a cross-section of the treatment tool 2 taken at a position of a line VI-VI illustrated in FIG. 4.

First, the connection relationship between the rotary knob 9 and the holder 112 will be explained.

At the end portion of the holder 112 on the distal end side Ar1, a pair of notch portions 1121 are arranged as illustrated in FIG. 5.

These pair of the notch portions 1121 are portions cut off from the distal end of the holder 112 toward the proximal end side Ar2, and are opposed to each other about the center axis Ax1. Hereinafter, for convenience of explanation, a pair of arc-shaped portions remaining after the pair of the notch portions 1121 are arranged at the end portion on the distal end side Ar1 of the holder 112 in the substantially cylindrical shape are denoted as arc portions 1122 (FIG. 4, FIG. 5).

Moreover, on an outer peripheral surface of the arc portion 1122, two protrusion portions 1123 that extend linearly from the distal end side Ar1 toward the proximal end side Ar2 are arranged as illustrated in FIG. 5.

On an inner peripheral surface of the rotary knob 9 in a substantially cylindrical shape, a connecting surface 91 to connect to the holder 112 is arranged as illustrated in FIG. 4 or FIG. 5.

The connecting surface 91 has a cross-sectional circular shape having an inner diameter substantially same as an outer diameter of the end portion of the holder 112 on the distal end side Ar1, and extends linearly along the center axis Ax1.

On this connecting surface 91, a pair of protruding portions 911 that protrude toward the center axis Ax1 from positions opposing to each other about the center axis Ax1, and that extend linearly along the center axis Ax1 are arranged. A width dimension (length in a vertical direction in FIG. 5) of these pair of protruding portions 911 is set to be substantially same as a width dimension (length in the vertical direction in FIG. 5) of the notch portion 1121. Hereinafter, for convenience of explanation, a pair of spaces having a cross-sectional arc shape surrounded by the connecting surface 91 and the pair of the protruding portions 911 are denoted as press fitting hole 912.

The holder 112 is connected to the rotary knob 9 as the pair of the arc portions 1122 are injected into the pair of the press fitting holes 912. At this time, the protrusion portion 1123 bites into the connecting surface 91. The rotary knob 9 and the holder 112 are thus integrally coupled with each other. That is, the rotary knob 9 and the holder 112 have no backlash therebetween, and relative rotation about the center axis Ax1 and relative movement along the center axis Ax1 are restricted.

In the present embodiment, the rotary knob 9 and the holder 112 are integrally coupled with each other by using press-fitting, but it is not limited thereto, and adhesion, screwing, or the like may be adopted as long as they can be integrally coupled with each other.

Furthermore, in the pair of the arc portions 1122, a first through hole 1124 that passes through in a direction perpendicular to the center axis Ax1 is arranged as illustrated in FIG. 3. Moreover, in the rotary knob 9, a second through hole 913 passing through in a direction perpendicular to the center axis Ax1 is arranged at a position opposing to the first through hole 1124.

To the first through hole 1124 and the second through hole 913, pins 92 are inserted as illustrated in FIG. 3. The pins 92 have a function of maintaining a relative positional relation between the rotary knob 9 and the holder 112 along the center axis Ax1.

Next, the connection relationship between the holder 112 and the slider rest 113 will be explained.

At the end portion of the slider rest 113 on the distal end side Ar1, a connection base 1131 is arranged as illustrated in FIG. 4 or FIG. 6.

The connection base 1131 has a planar shape, and is hanged between inner peripheral surfaces of the slider rest 11 straddling the center axis Ax1, in such a position that a plate surface is perpendicular to the center axis Ax1 (FIG. 6). To a portion of the connection base 1131 on the plate surface on the distal end side Ar1, an end portion of the inner pipe 111 on the proximal end side Ar2 is fixed.

In this connection base 1131, an insertion hole 1132 that passes through from front to back and that has a circular shape around the center axis Ax1 is arranged at a position on the center axis Ax1 as illustrated in FIG. 6. This insertion hole 1132 is a hole into which the vibration transmitting member 13 is inserted.

Furthermore, a pair of holes 1133 having a cross-sectional arc shape arranged between the inner peripheral surface of the slider rest 113 and the connection base 1131 function as holes into which the pair of arc portions 1122 are inserted, respectively, as illustrated in FIG. 6.

That is, as the pair of arc portions 1122 are respectively inserted in the pair of the holes 1133, the end portion of the slider rest 113 on the distal end side Ar1 is connected to the holder 112 in a state in which movement along the center axis Ax1 with respect to the holder 112 is allowed and rotation about the center axis Ax1 is restricted.

Next, the connection relationship between the rotary knob 9 and the slider rest 113 will be explained.

On the inner peripheral surface of the rotary knob 9 at a portion on the proximal end side relative to the connecting surface 91, which is the coupling position of the rotary knob 9 and the holder 112, a pair of first protruding portions 931 and a pair of second protruding portions 932 that protrude respectively out from the inner peripheral surface are arranged as illustrated in FIG. 6.

The pair of the first protruding portions 931 are aligned vertically in FIG. 6, maintaining a predetermined gap.

The pair of the second protruding portions 932 have shapes symmetrical with the pair of the first protruding portions 931 with respect to a plane passing through the center axis Ax1 and extending in the vertical direction in FIG. 6.

In the slider rest 113, on an outer peripheral surface at an end portion on the distal end side Ar1, a pair of insertion portions 1134 that are opposed to each other about the center axis Ax1 and that protrude out from the outer peripheral surface are arranged as illustrated in FIG. 6. One insertion portion 1134 out of the pair of the insertion portions 1134 is inserted into a portion between the pair of the first protruding portions 931. Moreover, the other one of the insertion portion 1134 out of the pair of the insertion portions 1134 is inserted in a portion between the pair of the second protruding portions 932. A width dimension (length in a vertical direction in FIG. 6) of the insertion portion 1134 is set to be substantially same as a separation distance between the pair of the first protruding portions 931.

That is, as the pair of the insertion portions 1134 are inserted in the portion between the pair of the first protruding portions 931 and in the portion between the pair of the second protruding portions 932, the end portion of the slider rest 113 on the distal end side Ar1 is connected to the holder in a state in which movement along the center axis Ax 1 with respect to the holder is allowed and rotation about the center axis Ax1 is restricted.

By the connection relationship described above, the slider rest 113 transmits a force according to rotation of the rotary knob 9 to the holder 112 at the distal end side Ar2 relative to the coupling position (connecting surface 91) of the rotary knob 9 and the holder 112.

[About Attachment Mechanism of Rotary knob and Holder to Casing Body]

Next, an attachment mechanism of the rotary knob 9 to the casing body 61 and an attachment mechanism of the holder 112 to the casing body 61 will be sequentially explained.

Figure 7:
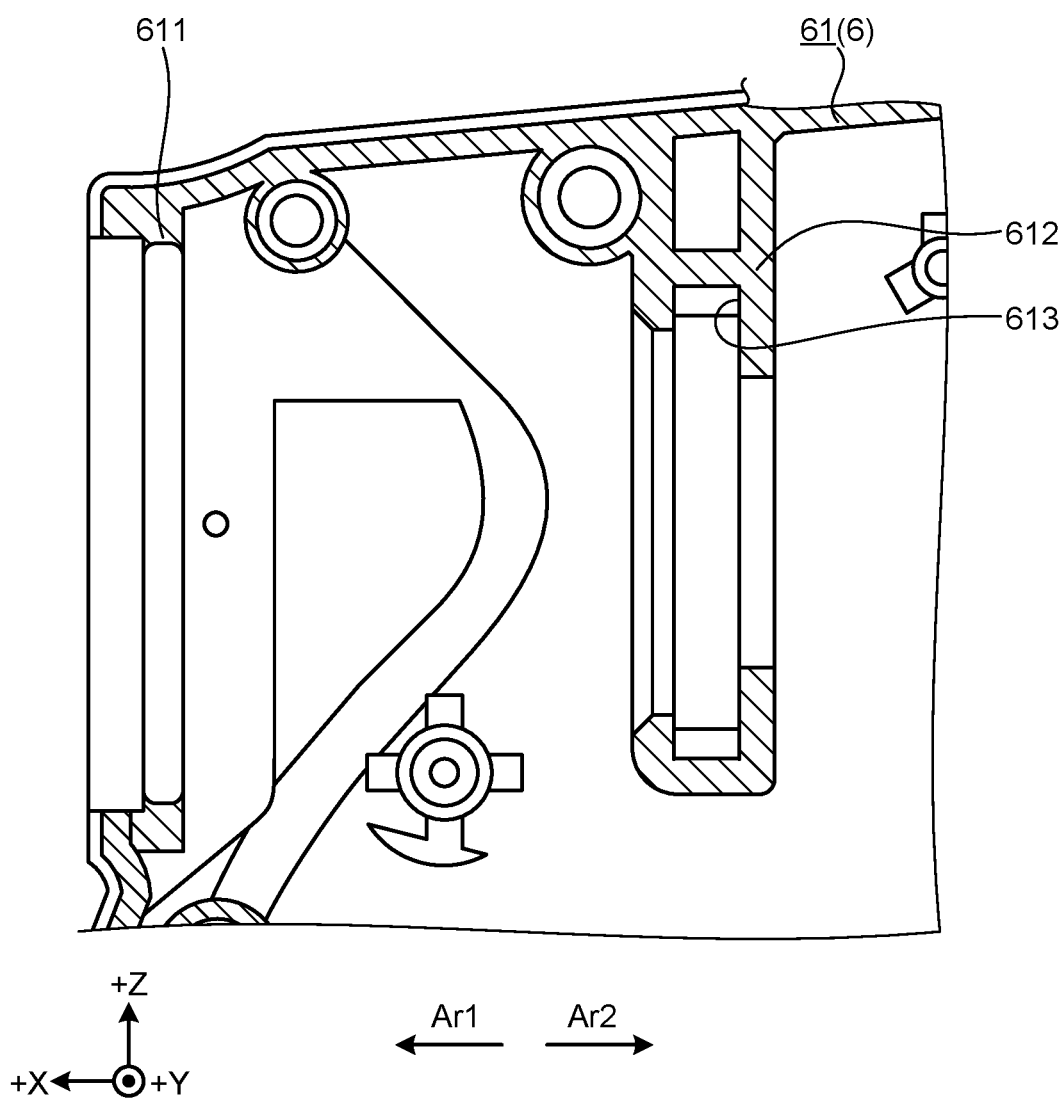
FIG. 7 is a diagram explaining an attachment mechanism of the rotary knob and the holder with respect to a casing body.

FIG. 7 is a diagram explaining the attachment mechanism of the rotary knob 9 and the holder 112 to the casing body 61. Specifically, FIG. 7 is a cross-section corresponding to FIG. 3.

First, the attachment mechanism of the rotary knob 9 to the casing body 61 will be explained.

In the rotary knob 9, on an outer peripheral surface of an end portion on the proximal end side Ar2, a ring-shaped concave portion 94 that recesses toward the center axis Ax1 and that extend along a circumferential direction about the center axis Ax1 is arranged as illustrated in FIG. 3.

On an inner surface of the casing body 61, a ring-shaped first protrusion portion 611 that protrudes toward the center axis Ax1 and that extends along the circumferential direction about the center axis Ax1 is arranged as illustrated in FIG. 3 or FIG. 7.

As the first protrusion portion 611 is arranged inside the concave portion 94, the rotary knob 9 is attached to the casing body 61. At this time, as a protrusion end of the first protrusion portion 611 abuts on a bottom surface of the concave portion 94, the rotary knob 9 is positioned with respect to the casing body 61 in the radial direction about the center axis Ax1. A location of the rotary knob 9 is fixed relative to the casing body 61 in the radial direction about the center axis Ax1. A side surface of the first protrusion portion 611 and a side surface of the concave portion 94 do not abut on each other. That is, the first protrusion portion 611 and the concave portion 94 do not have a function of positioning the rotary knob 9 with respect to the casing body 61 in the direction along the center axis Ax1.

Next, the attachment mechanism of the holder 112 with respect to the casing body 61 will be explained.

In the holder 112, on an outer peripheral surface of an end portion on the proximal end side Ar2, a disc-shaped flange 1125 that protrudes from the outer peripheral surface and that extends along the circumferential direction about the center axis Ax1 is arranged as illustrated in FIG. 3. This flange 1125 is positioned on the proximal end side Ar2 relative to the proximal end of the rotary knob 9 and the slider rest 113.

On the inner surface of the casing body 61, at a position on the proximal end side Ar2 relative to the first protrusion portion 611, a ring-shaped second protrusion portion 612 that protrudes toward the center axis Ax1 and that extends along the circumferential direction about the center axis Ax1 is arranged as illustrated in FIG. 3 or FIG. 7. Moreover, on the inner peripheral surface of the second protrusion portion 612, a ring-shaped slot 613 that recesses in a direction separating from the center axis Ax1 and that extends along the circumferential direction about the center axis Ax1 is arranged.

As the flange 112S is arranged inside the slot 613, the holder 112 is attached to the casing body 61. At this time, as the flange 112S is sandwiched between side surfaces of the slot 613, the holder 112 is positioned with respect to the casing body 61 in the direction along the center axis Ax1. A location of the holder 112 is fixed relative to the casing body 61 along a longitudinal axis of the vibration transmitting member 13. Moreover, as a protrusion end of the second protrusion portion 612 abuts on a portion on the outer peripheral surface of the holder 112 on the proximal end side relative to the flange 112S, the holder 112 is positioned with respect to the casing body 61 in the radial direction about the center axis Ax1. The holder 112 is positioned radially relative to the longitudinal axis. A location of the holder 112 is fixed relative to the casing body 61 in the radial direction about the center axis Ax1.

According to the present embodiment explained above, following effects are produced.

In the treatment tool 2 according to the present embodiment, the rotary knob 9 and the holder 112 are integrally coupled with each other. Therefore, it is unnecessary to perform positioning of each of the rotary knob 9 and the holder 112 with respect to the casing body 61 in the direction along the center axis Ax1 and in the radial direction about the center axis Ax1. In the present embodiment, out of the rotary knob 9 and the holder 112, the holder 112 is positioned with respect to the casing body 61 in the direction along the center axis Ax1. A location of the holder 112 is fixed relative to the casing body 61 along the longitudinal axis of the vibration transmitting member 13. Moreover, both of the rotary knob 9 and the holder 112 are positioned with respect to the casing body 61 in the radial direction about the center axis Ax1. In other words, both of the rotary knob 9 and the holder 112 are positioned radially relative to the longitudinal axis. Locations of both of the rotary knob 9 and the holder 112 are fixed relative to the casing body 61 in the radial direction about the center axis Ax1. That is, a structure in which backlashes of the rotary knob 9 and the holder 112 with respect to the casing body 61 are reduced, and in which sliding surfaces between the casing body 61, and the rotary knob 9 and the holder 112 are less prone to change is provided. In other words, a structure in which the sliding resistance at the time of rotating the rotary knob 9 is less prone to change is obtained.

Therefore, according to the treatment tool 2 according to the present embodiment, the operating force at the time of rotating the rotary knob 9 can be stabilized.

Particularly, both of rotary knob 9 and the holder 112 are positioned with respect to the casing body 61 in the radial direction about the center axis Ax1. In other words, both of the rotary knob 9 and the holder 112 are positioned radially relative to the longitudinal axis. Locations of the rotary knob 9 and the holder 112 are fixed relative to the casing body 61 in the radial direction about the center axis Ax1. Therefore, the rotary knob 9 and the holder 112 are not to be held in a cantilever manner with respect the casing body 61, and the rotary knob 9 can be rotated in a stable state.

Moreover, in the treatment tool 2 according to the present embodiment, the pins 92 to maintain the relative positional relationship along the center axis Ax1 between rotary knob 9 and the holder 112 are arranged. Therefore, by the pins 92, relative position deviation along the center axis Ax1 between the rotary knob 9 and the holder 112 with time can be prevented.

Furthermore, in the treatment tool 2 according to the present embodiment, the slider rest 113 abuts on the holder 112 on the proximal end side Ar2 relative to the coupling position (the connecting surface 91) of the rotary knob 9 and the holder 112, and transmits a force according to rotation from the rotary knob 9 to the holder 112. That is, when transmitting the force according to the rotation from the rotary knob 9 to the holder 112, the force is not to be concentrated at the coupling position (the connecting surface 91), but can be distributed to the pathway of the rotary knob 9, the slider rest 113, to the holder 112. Therefore, the connection strength between the rotary knob 9 and the holder 112 at the coupling position can be maintained favorably.

Furthermore, the treatment tool 2 according to the present embodiment is enable to apply a high frequency energy to a target site, besides an ultrasonic energy. In the holder having electrical insulation, the electrically communication path P1 that is electrically connected to the jaw 12 through the shaft 10 to flow a high frequency current is arranged. Therefore, by the holder 112, a short circuit between the vibration transmitting member 13 and the electrically communication path P1 can be prevented.

OTHER EMBODIMENTS

The embodiment to implement the present disclosure has so far been explained, but the present disclosure is not to be limited only to the embodiment described above.

In the embodiment described above, a configuration to apply both an ultrasonic energy and a high frequency energy to a target site is adopted as the ultrasound treatment tool according to the present disclosure, but not limited thereto, a configuration to apply only the ultrasonic energy may be adopted. Moreover, a configuration to apply at least either one of a high frequency energy and a thermal energy other than the ultrasonic energy to a target site may be adopted. "Applying a thermal energy to a target site" means transmitting a heat generated by a heater or the like to a target site.

The electrically conductive material of the shaft 10, the jaw 12 and the electrically communication path P1 may be applied same conductive material or different conductive material from each other. Any combinations of conductive materials may be applied.

In the embodiment described above, out of the rotary knob 9 and the holder 112, the holder 112 is positioned with respect to the casing body 61 in the direction along the center axis Ax1. A location of the holder 112 is fixed relative to the casing body 61 along the longitudinal axis of the vibration transmitting member 13, but it is not limited thereto. For example, out of the rotary knob 9 and the holder 112, the rotary knob 9 may be positioned with respect to the casing body 61 in the direction along the center axis Ax1. A location of the rotary knob 9 may be fixed relative to the casing body 61 in the direction along the center axis Ax1.

First Modification

In the embodiment described above, a configuration according to a first modification described below may be adopted.

Figure 8:
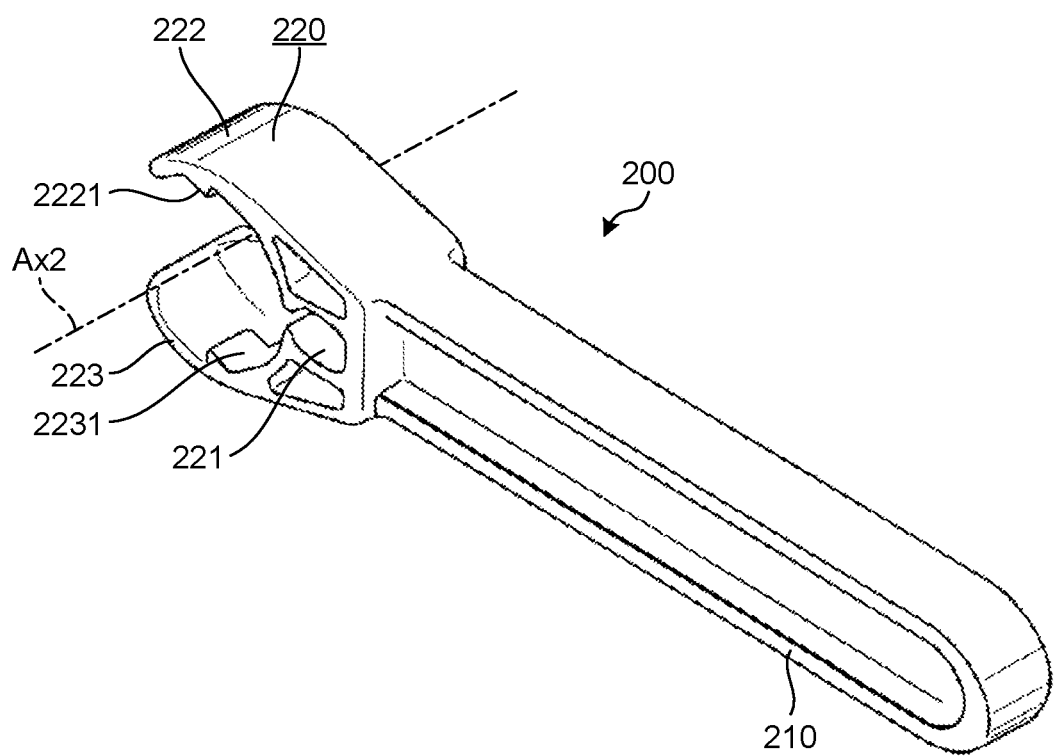
FIG. 8 is a diagram explaining a first modification of the embodiment.

FIG. 8 to FIG. 15 are diagrams explaining the first modification of the present embodiment. Specifically, FIG. 8 is a perspective view of a torque wrench 200.

Hereinafter, for convenience of explanation, a conventional rotary knob is denoted as rotary knob 300. Moreover, a rotary knob according to the first modification is denoted as rotary knob 300A.

Figure 9:
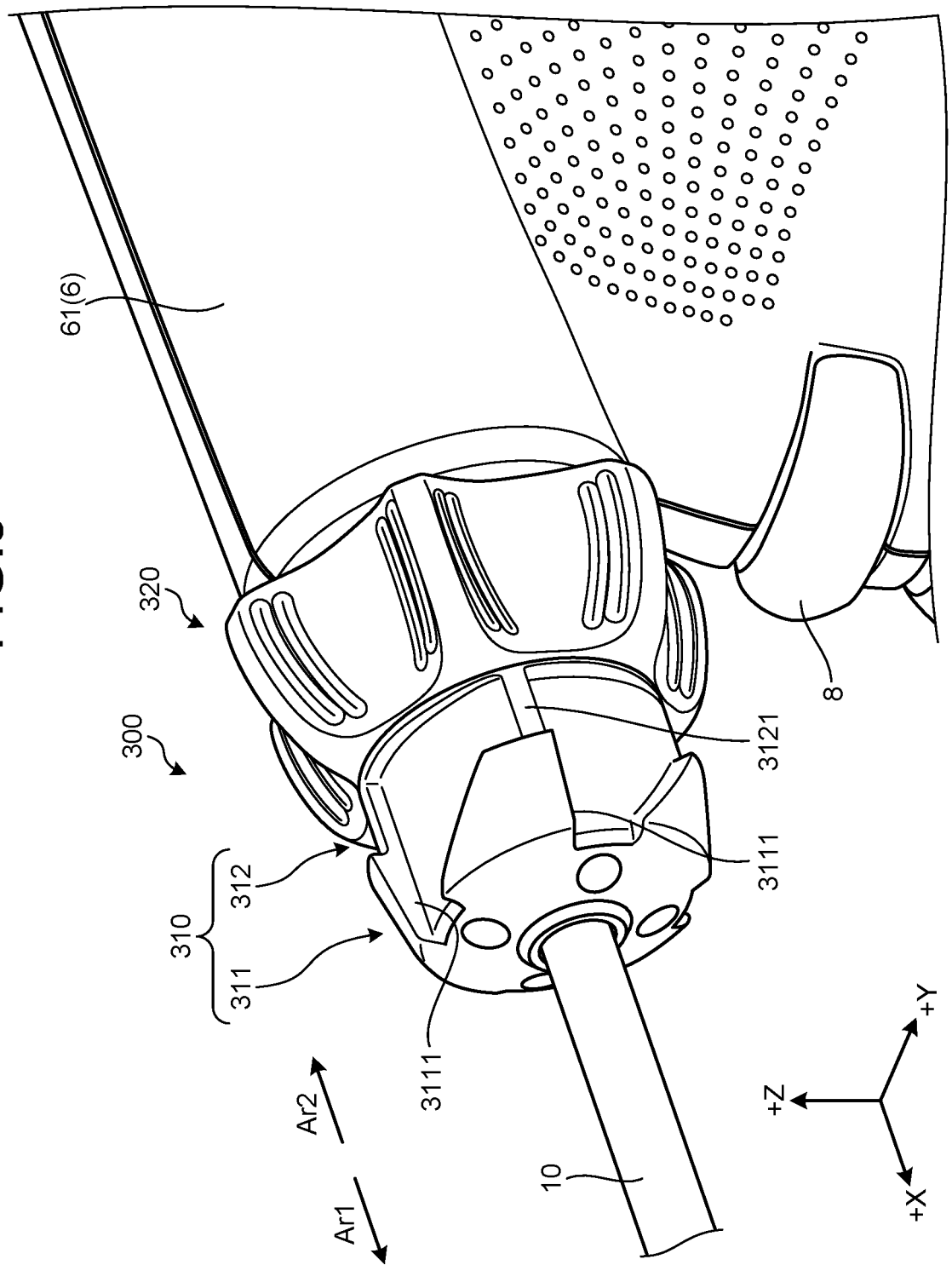
FIG. 9 is a diagram explaining the first modification of the embodiment.
Figure 10:
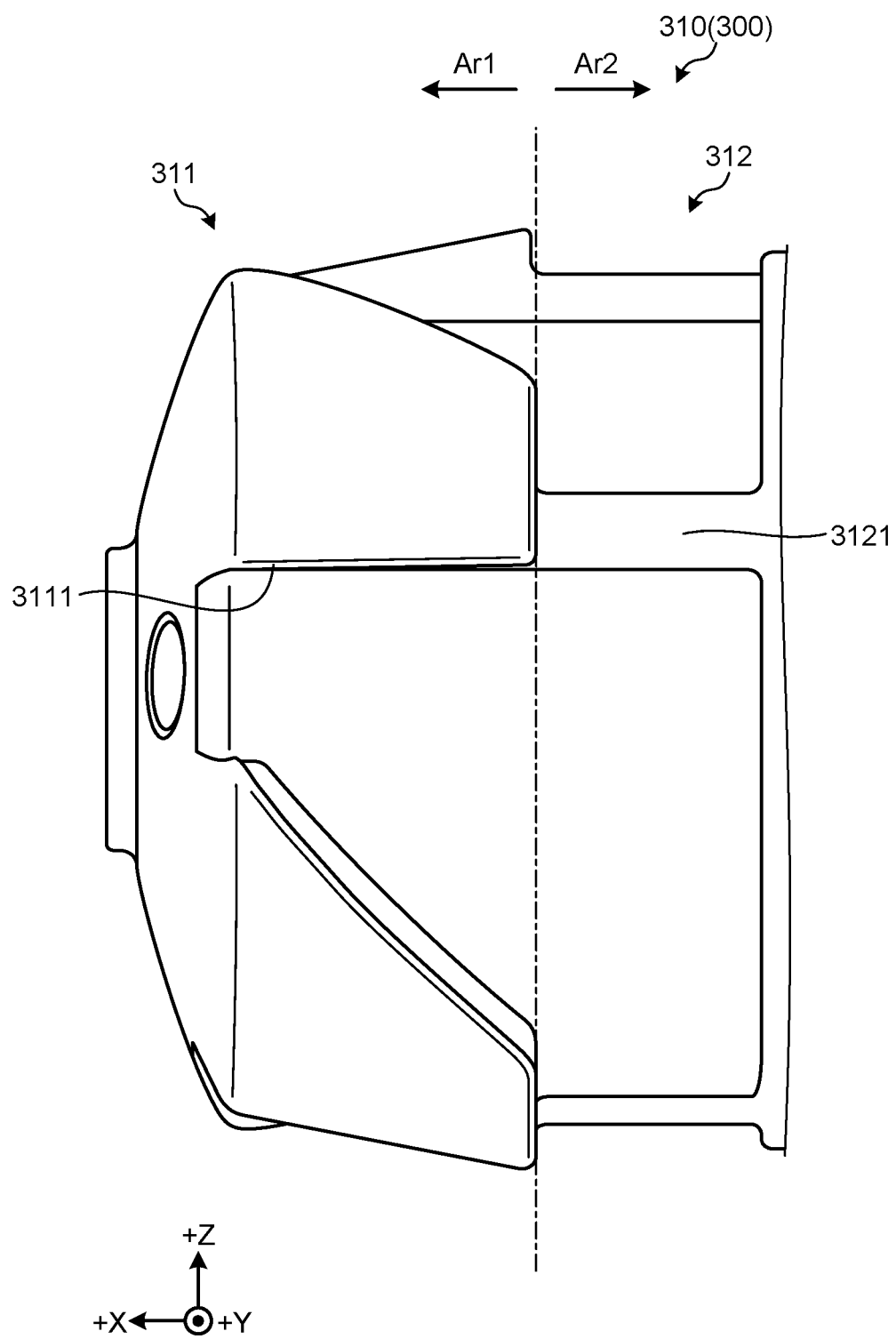
FIG. 10 is a diagram explaining the first modification of the embodiment.
Figure 11:
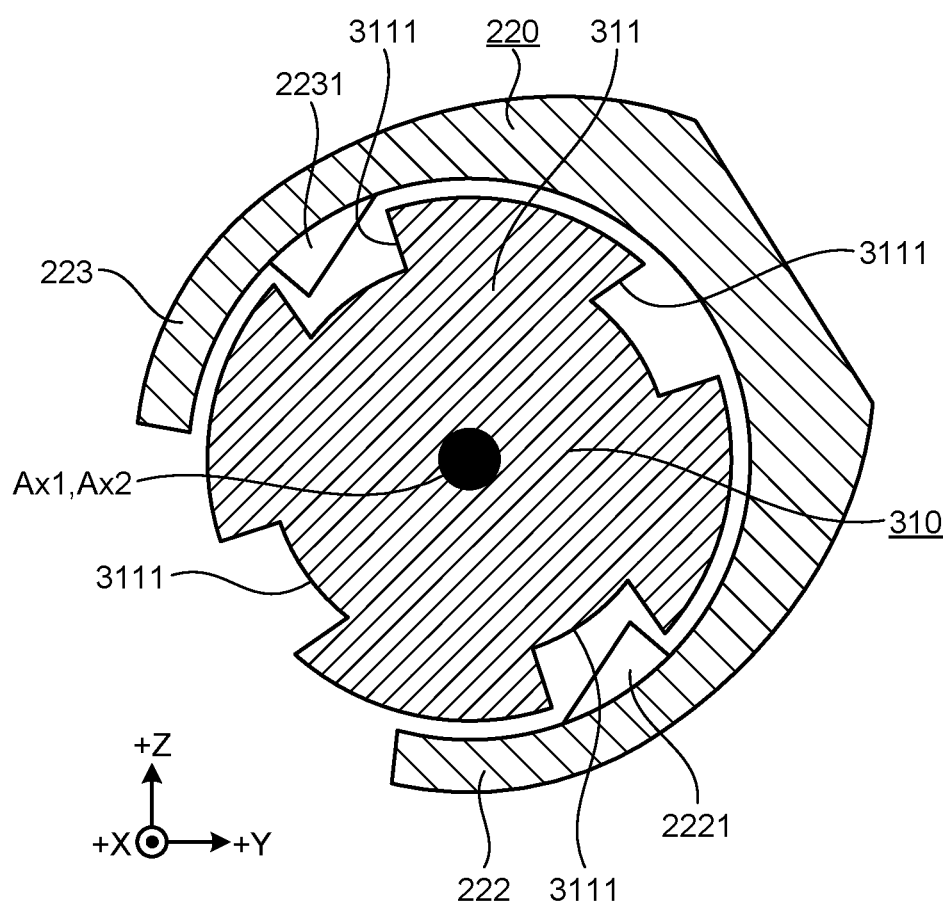
FIG. 11 is a diagram explaining the first modification of the embodiment.
Figure 12:
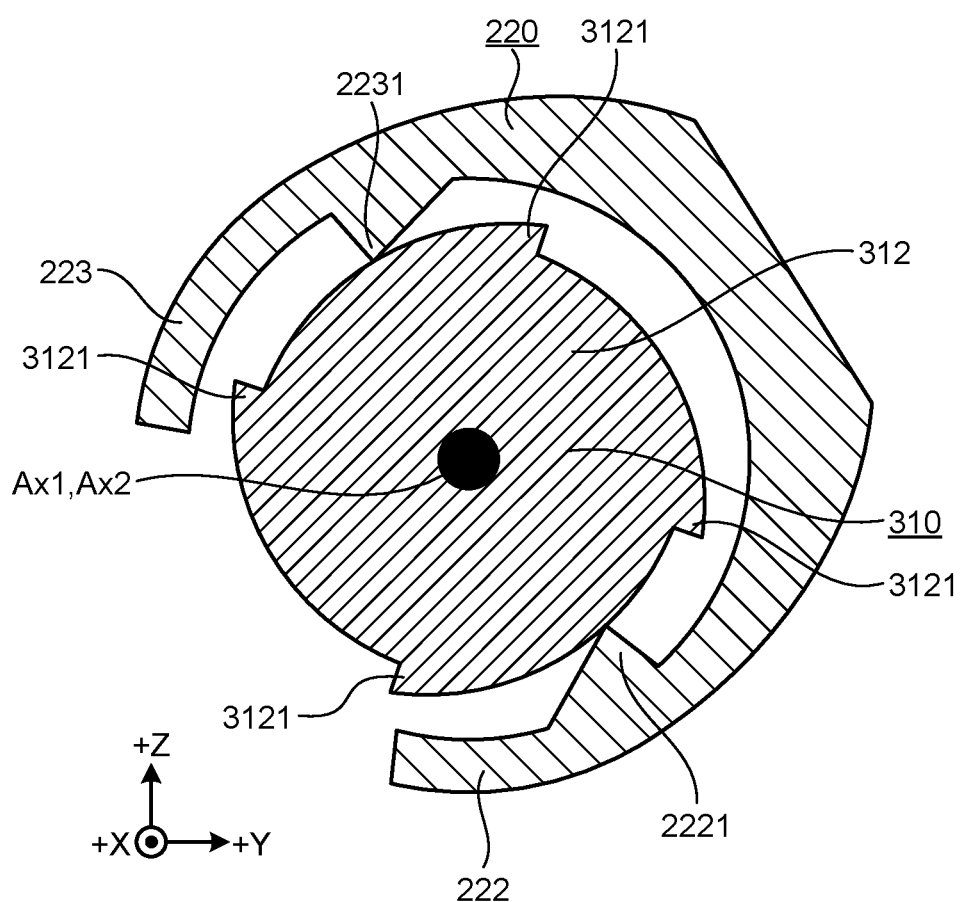
FIG. 12 is a diagram explaining the first modification of the embodiment.
Figure 13:
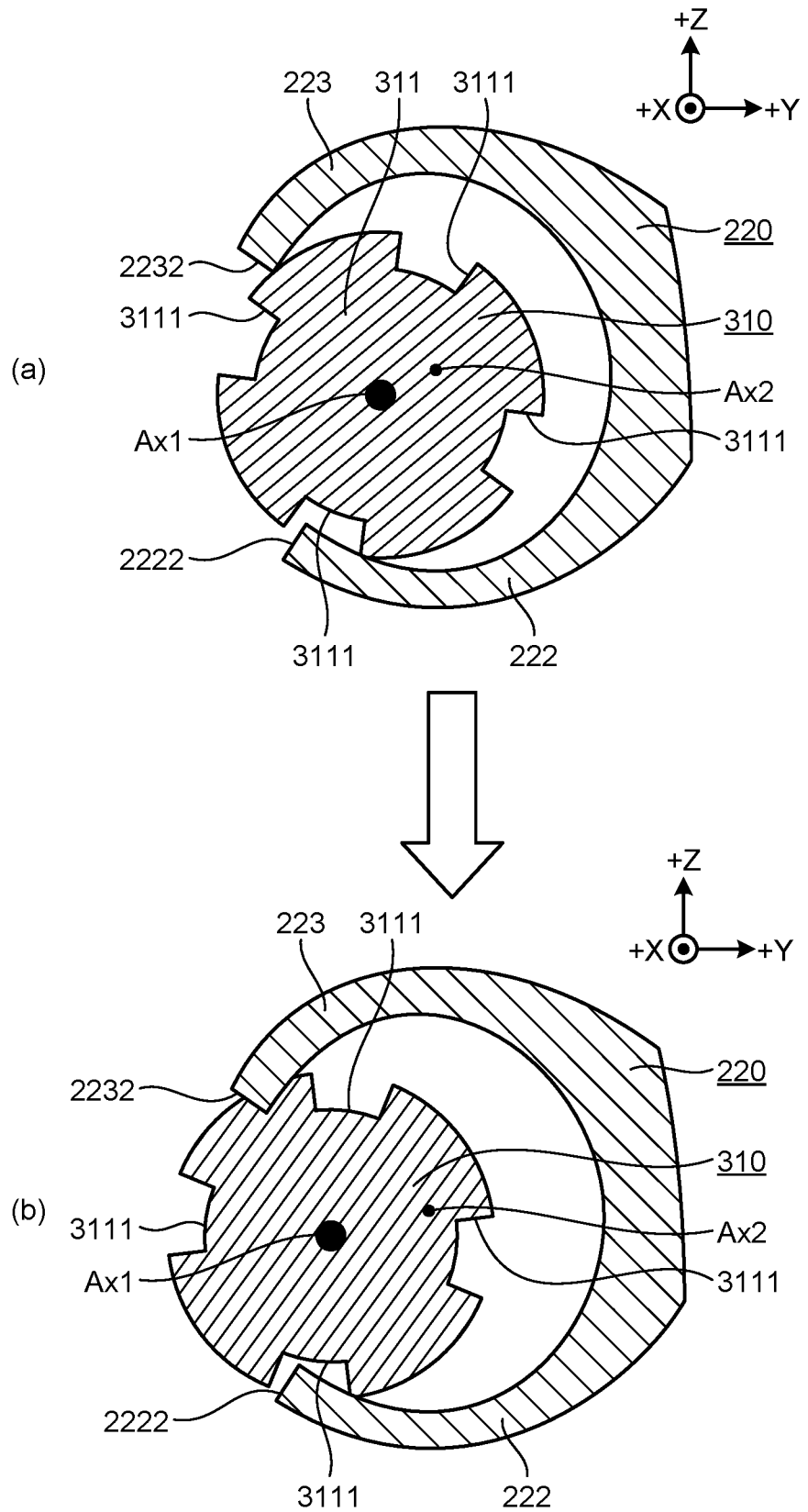
FIG. 13 is a diagram explaining the first modification of the embodiment.

FIG. 9 to FIG. 13 are diagrams explaining the conventional knob 300. Specifically, FIG. 9 is a perspective view of the rotary knob 300. FIG. 10 is a diagram illustrating only an engaged portion 310 constituting the rotary knob 300 viewed from the +Y axis side. FIG. 11 illustrates a cross-section taken along a plane passing through a first engaged portion 311 in a state in which the torque wrench 200 is engaged with the engaged portion 310, viewed from the distal end side Ar1. FIG. 12 illustrates a cross-section taken along a plane passing through a second engaged portion 312 in a state in which the torque wrench 200 is engaged with the engaged portion 310, viewed from the distal end side Ar1. FIG. 13 is a cross-section corresponding to FIG. 11, and is a diagram explaining a problem of the conventional rotary knob 300.

Figure 14:
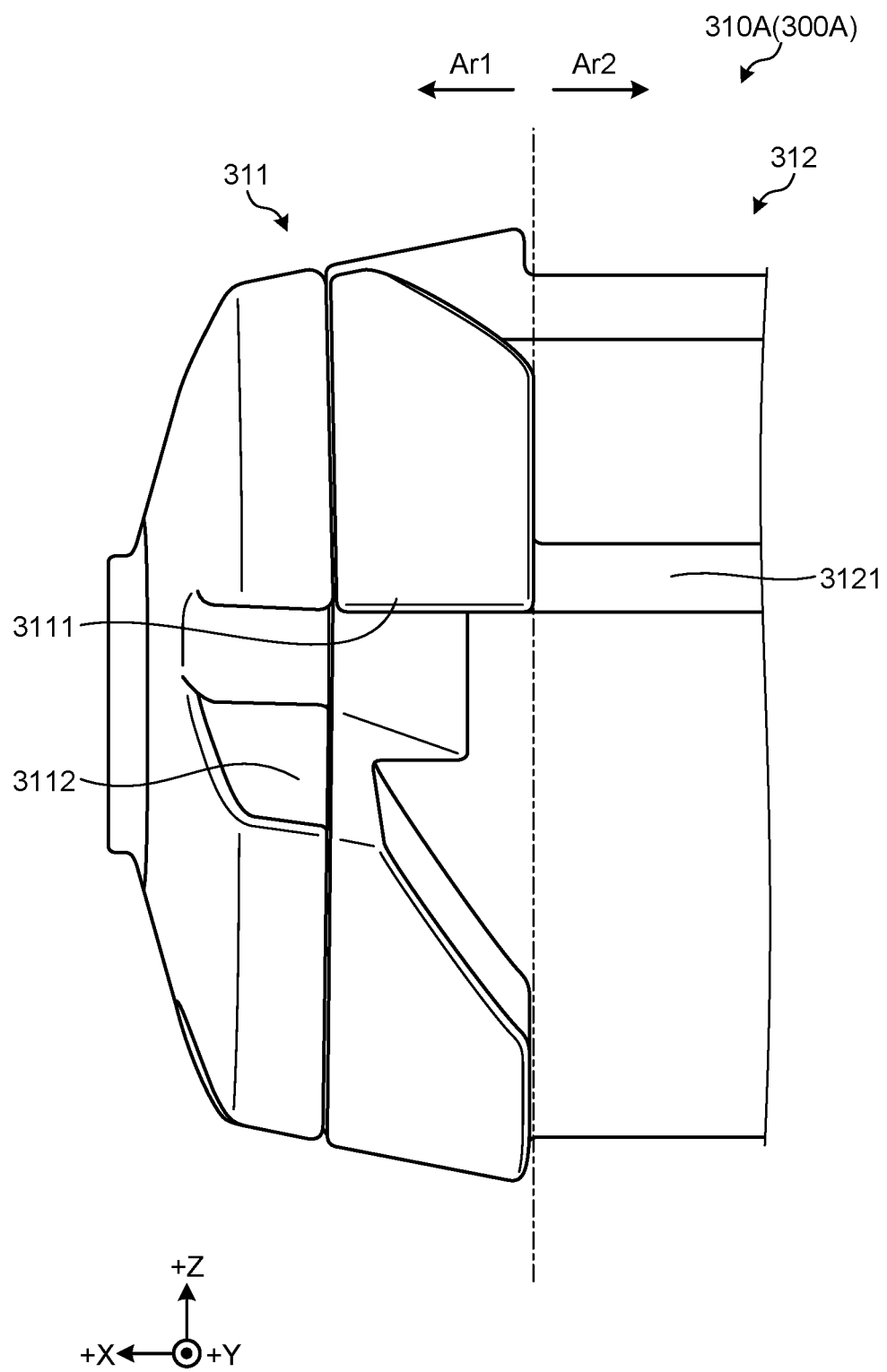
FIG. 14 is a diagram explaining the first modification of the embodiment.
Figure 15:
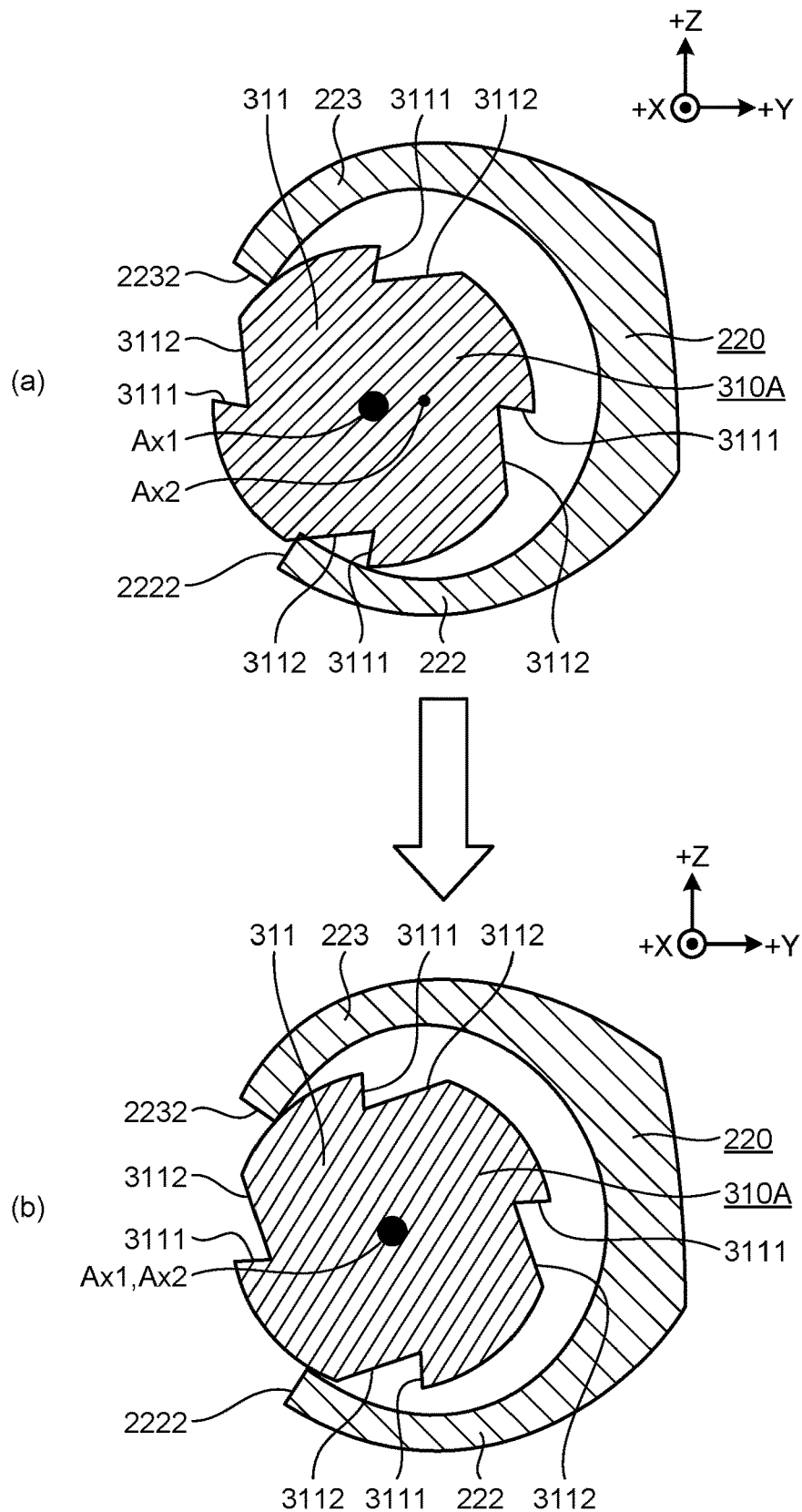
FIG. 15 is a diagram explaining the first modification of the embodiment.

On the other hand, FIG. 14 and FIG. 15 are diagrams explaining the rotary knob 300A according to the first modification. Hereinafter, for convenience of explanation, an engaged portion constituting the rotary knob 300A according to the first modification is denoted as engaged portion 310A. Specifically, FIG. 14 is a diagram corresponding to FIG. 10. FIG. 15 is a cross-section corresponding to FIG. 13, and is a diagram explaining an effect of the rotary knob 300A according to the first modification.

Conventionally, for screwing of the external thread 521 with the internal thread 132, that is, connection of the vibration transmitting member 13 and the ultrasound vibrator 52 to each other, the torque wrench 200 illustrated in FIG. 8 is used.

The torque wrench 200 is made from, for example, a resin material, to form a straight arm 210 being an operating portion and a head 220 for rotation torque transmission that is arranged at one end of the arm 210 into one piece as illustrated in FIG. 8. Not limited to the resin material, the torque wrench 200 may be made from a metal or the like.

The head 220 has a cylindrical shape enabled to cover the entire outer peripheral surface of the engaged portion 310 constituting the rotary knob 300. Hereinafter, for convenience of explanation, a center axis of the head 220 is denoted as center axis Ax2 (FIG. 8). Moreover, in the head 220, a slit 221 extending along the center line of the arm 210 is arranged. This slit 221 cuts off a portion of a side wall off the head 220 in the cylindrical shape. That is, a portion of a cylinder is cut off by the slit 221, and the head 220 thereby has a C-shape having a pair of cross-sectional arc shaped portions. Hereinafter, for convenience of explanation, the pair of the cross-sectional arc-shaped portions are denoted as first and second engagement arms 222, 223.

On the inner peripheral surface of the first engagement arm 222, a first protrusion portion 2221 that protrudes out from the inner peripheral surface toward the center axis Ax2 is arranged as illustrated in FIG. 8. This first protrusion portion 2221 is arranged only in an area (area on a left side in FIG. 8) when the head 220 is divided in to two area by a plane perpendicular to the center axis Ax2.

Moreover, on the inner peripheral surface of the second engagement arm 223, a second protrusion portion 2231 that protrudes from the inner peripheral surface toward the center axis Ax2 is arranged at a position opposing to the first protrusion portion 2221 about the center axis Ax2 as illustrated in FIG. 8. This second protrusion portion 2231 is also arranged only in one area in which the first protrusion portion 2221 is arranged when the head 220 is divided into two areas by a plane perpendicular to the center axis Ax2, similarly to the first protrusion portion 2221.

The first and the second protrusion portions 2221, 2231 described above corresponds to a claw portion according to the present disclosure.

The rotary knob 300 includes the engaged portion 310, and a rotation operating portion 320 (FIG. 9) that accepts a rotation operation performed by the operator, such as surgeon, as illustrated in FIG. 9 to FIG. 12. The engaged portion 310 is a portion that is arranged in the portion of the rotary knob 300 on the distal end side Ar1 (FIG. 9), that engages with the torque wrench 200, and that is used to connect the vibration transmitting member 13 and the ultrasound vibrator 52 to each other. This engaged portion 310 includes the first engaged portion 311 (FIG. 9 to FIG. 11) and the second engaged portion 312 (FIG. 9, FIG. 10, FIG. 12) as illustrated in FIG. 9 to FIG. 12.

The first engaged portion 311 is arranged in a portion of the engaged portion 310 on the distal end side Ar1 (FIG. 9, FIG. 10), and is a portion that does not engage with the torque wrench 200 when connecting the vibration transmitting member 13 and the ultrasound vibrator 52 with each other. This first engaged portion 311 is positioned on the center axis Ax1, and has a cylindrical column shape extending linearly along the center axis Ax1. An outer diameter of the first engaged portion 311 is set to be a little smaller than an inner diameter of the head 220.

In this first engaged portion 311, on an outer peripheral surface, a groove portion 3111 that recesses from the outer peripheral surface, and that passes through from a distal end to a proximal end of the first engaged portion 311 is arranged as illustrated in FIG. 9 to FIG. 11. In the conventional rotary knob 300, the groove portion 3111 is arranged at each of 90° rotation-symmetrical positions about the center axis Ax1 on the outer peripheral surface of the first engaged portion 311. That is, four units of the groove portions 3111 are arranged. Moreover, the groove portion 3111 has a cross-sectional rectangular shape as illustrated in FIG. 11. An outer diameter at a bottom surface of the groove portion 3111 is set to be a little smaller than a separation distance between a protrusion end of a first protrusion portion 2221 (the second protrusion portion 2231) and the center axis Ax2.

The second engaged portion 312 is a portion that is positioned between the first engaged portion 311 and the rotation operating portion 320 (FIG. 9, FIG. 10), and that engages with the torque wrench 200 when connecting the vibration transmitting member 13 and the ultrasound vibrator 52 with each other. In this second engaged portion 312, an engaging portion 3121 is arranged as illustrated in FIG. 12.

Specifically, an outer peripheral surface of the second engaged portion 312 has an outer diameter gradually increasing along a clockwise direction about the center axis Ax1 in FIG. 12 from a position to which the bottom surface of the groove portion 3111 is extended linearly toward the proximal end side Ar2 along the center axis Ax1. The outer peripheral surface is formed to suddenly become as small as an outer diameter at the bottom surface of the groove portion 3111 at the position of the engaging portion 3121. That is, the engaging portion 3121 is arranged as many as the number of groove portions 3111.

When the vibration transmitting member 13 and the ultrasound vibrator 52 are connected to each other, an operator performing the connection operates the torque wrench 200 as described below.

Specifically, the operator places the first and the second protrusion portions 2111, 2231 at the groove portions 3111, respectively while keeping the torque wrench 200 in a position in which the one area described above is directed toward the proximal end side Ar2 relative to the other area. The operator then moves the torque wrench 200 to the proximal end side Ar2 in a state in which the first and the second protrusion portions 2221, 2231 pass through the groove portions 3111 (state illustrated in FIG. 11).

Thereafter, the operator rotates the torque wrench 200 in a clockwise direction in FIG. 12 about the center axis Ax1, Ax2. When the torque wrench 200 is rotated, the first and the second engagement arms 222, 223 elastically deformed in a direction separating from the center axes Ax1, Ax2 because the first and the second protrusion portions 2221, 2231 slide on the outer peripheral surface of the second engaged portion 312. The rotary knob 300 then rotates with rotation of the torque wrench 200. The first and the second engagement arms 222, 223 return to their original form when the first and the second protrusion portions 2221, 22231 move over the engaging portion 3121.

By the operation described above, the rotary knob 300 (the vibration transmitting member 13) is rotated, and the internal thread 132 is screwed in the external thread 521 with desirable torque. Thus, the vibration transmitting member 13 and the ultrasound vibrator 52 are connected to each other.

The center axes Ax1, Ax2 correspond to a rotation center axis according to the present disclosure.

In the conventional rotary knob 300 explained above, there are problems described below.

Out of end portions 2222, 2232 (FIG. 13) in a circumferential direction about the center axis Ax2 in the first and the second engagement arms 222, 223, an end portion that protrudes along the rotation direction of the torque wrench 200 by the operation of the operator is the end portion 2222.

For example, depending on an operation of the operator, the center axis Ax2 becomes misaligned with respect to the center axis Ax1 as illustrated in (a) of FIG. 13, and the end portion 2222 can enter the groove portion 3111. If the operation is continued in such a state, the center axis Ax2 further deviates from the center axis Ax1 as illustrated in (b) of FIG. 13, and the internal thread 132 cannot be screwed with the external thread 521 with desirable torque. That is, the vibration transmitting member 13 and the ultrasound vibrator 52 cannot be connected to each other appropriately.

In the rotary knob 300A according to the first modification, to solve the problem described above, a slanted surface 3112 is arranged in all of the groove portions 3111 as illustrated in FIG. 14.

Specifically, the slanted surface 3112 is a slanted surface that is arranged on a side surface of the groove portion 3111, and that formed such that the diameter about the center axis Ax1 gradually increases along the rotation direction (clockwise direction in FIG. 15) of the rotary knob 300A according to the rotation direction of the torque wrench 200.

According to the first modification explained above, following effects are produced.

Also in the rotary knob 300A according to the first modification, the center axis Ax2 can be misaligned with respect to the center axis Ax1 as illustrated in (a) of FIG. 15, for example, depending on an operation by the operator, and the end portion 2222 can enter the groove portion 3111, similarly to the conventional rotary knob 300. However, in the rotary knob 300A according to the first modification, when the operation is continued in such a state, the end portion 2222 is guided to the outer peripheral surface of the first engaged portion 311 along the slanted surface 3112 as illustrated in (b) of FIG. 15, and the center axes Ax1 and Ax2 match with each other. That is, also in such a state, the internal thread 132 can be screwed with the external thread 521 with desirable torque, and the vibration transmitting member 13 and the ultrasound vibrator 52 can be connected to each other appropriately.

Second Modification

In the embodiment described above, a configuration according to a second modification described below may be adopted.

Hereinafter, for convenience of explanation, a rotary knob and an engaged portion according to the second modification are denoted as rotary knob 300B and engaged portion 310B. Moreover, a torque wrench and a head according to the second modification are denoted as torque wrench 200B and head 220B, respectively.

Figure 16:
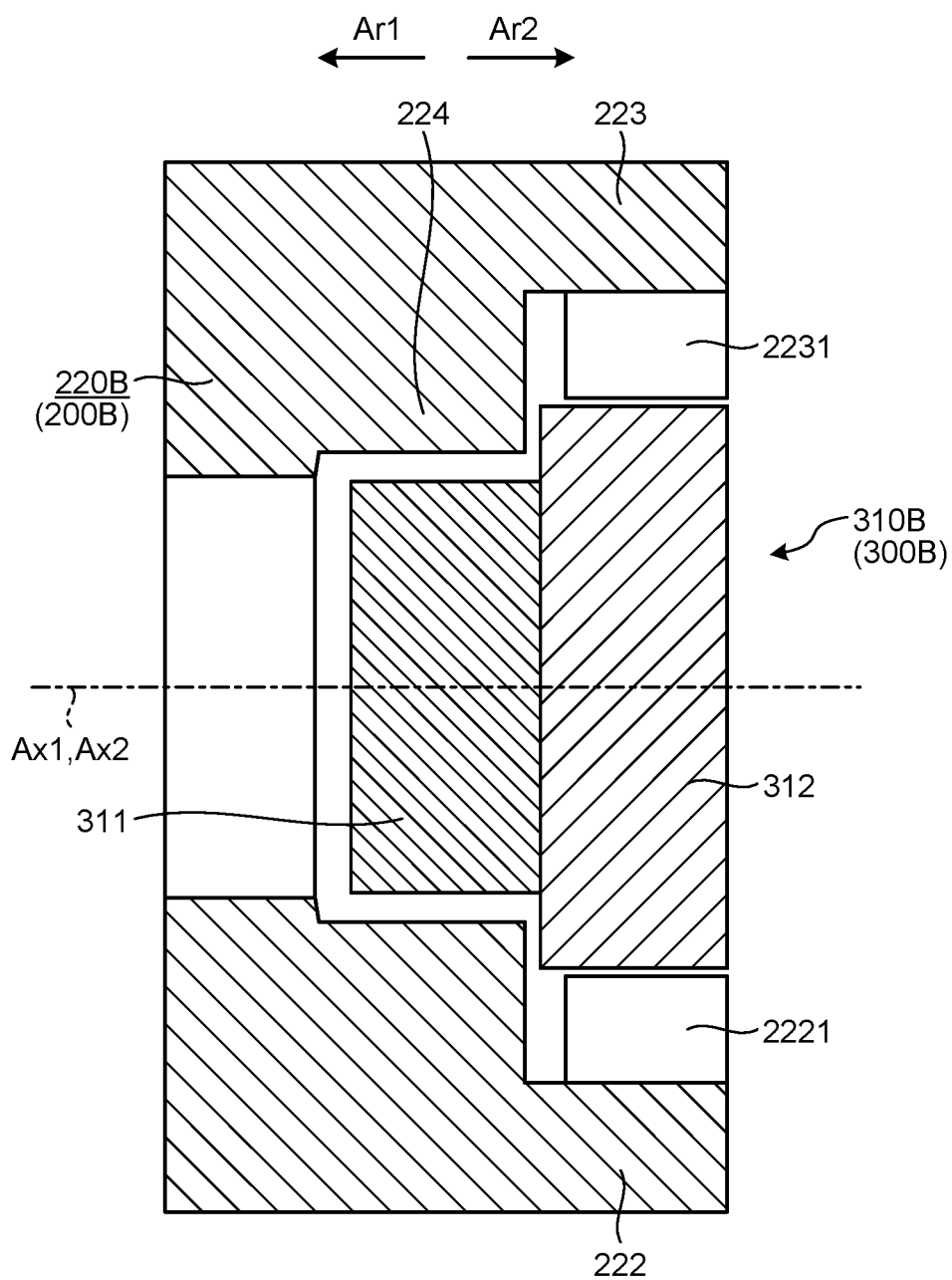
FIG. 16 is a diagram explaining a second modification of the embodiment.

FIG. 16 is a diagram explaining the second modification of the embodiment. Specifically, FIG. 16 is a cross-section taken along a plane along the center axis Ax1 in a state in which the torque wrench 200B is engaged with the rotary knob 300A.

In the rotary knob 300B according to the second modification, a shape of the first engaged portion 311 is changed from the rotary knob 300A explained in the first modification described above.

Specifically, in the first engaged portion 311 according to the second modification, the outer diameter is set to be smaller than a distance between the protrusion end of the first protrusion portion 2221 (second protrusion portion 2231) and the center axis Ax2 as illustrated in FIG. 16. That is, in the first engaged portion 311, the groove portion 3111 explained in the first modification described above is omitted.

Moreover, in the torque wrench 200B according to the second modification, an inner peripheral surface of the head 220B has a shape described below.

When the head 220B is divided into two areas by a plane perpendicular to the center axis Ax2, an inner diameter of an internal peripheral surface of an area 224 other than one area in which the first and the second protrusion portions 2221, 2231 are arranged is set to be a little larger than the outer diameter of the first engaged portion 311 as illustrated in FIG. 16.

Also when the rotary knob 300B according to the second modification explained above is adopted, entrance of the end portion 2222 into the groove portion 3111 can be avoided, and misalignment of the center axes Ax1, Ax2 can be suppressed by the other area 224 at the time of operation of the torque wrench 200B. Therefore, an effect similar to that of the first modification described above is produced.

Third Modification

In the embodiment described above, a configuration according to a third modification described below can be adopted.

Hereinafter, for convenience of explanation, a rotary knob and an engaged portion according to the third modification are denoted as rotary knob 300C and engaged portion 310C, respectively. Moreover, a torque wrench and a head according to the second modification are denoted as torque wrench 200C and head 200C, respectively.

Figure 17:
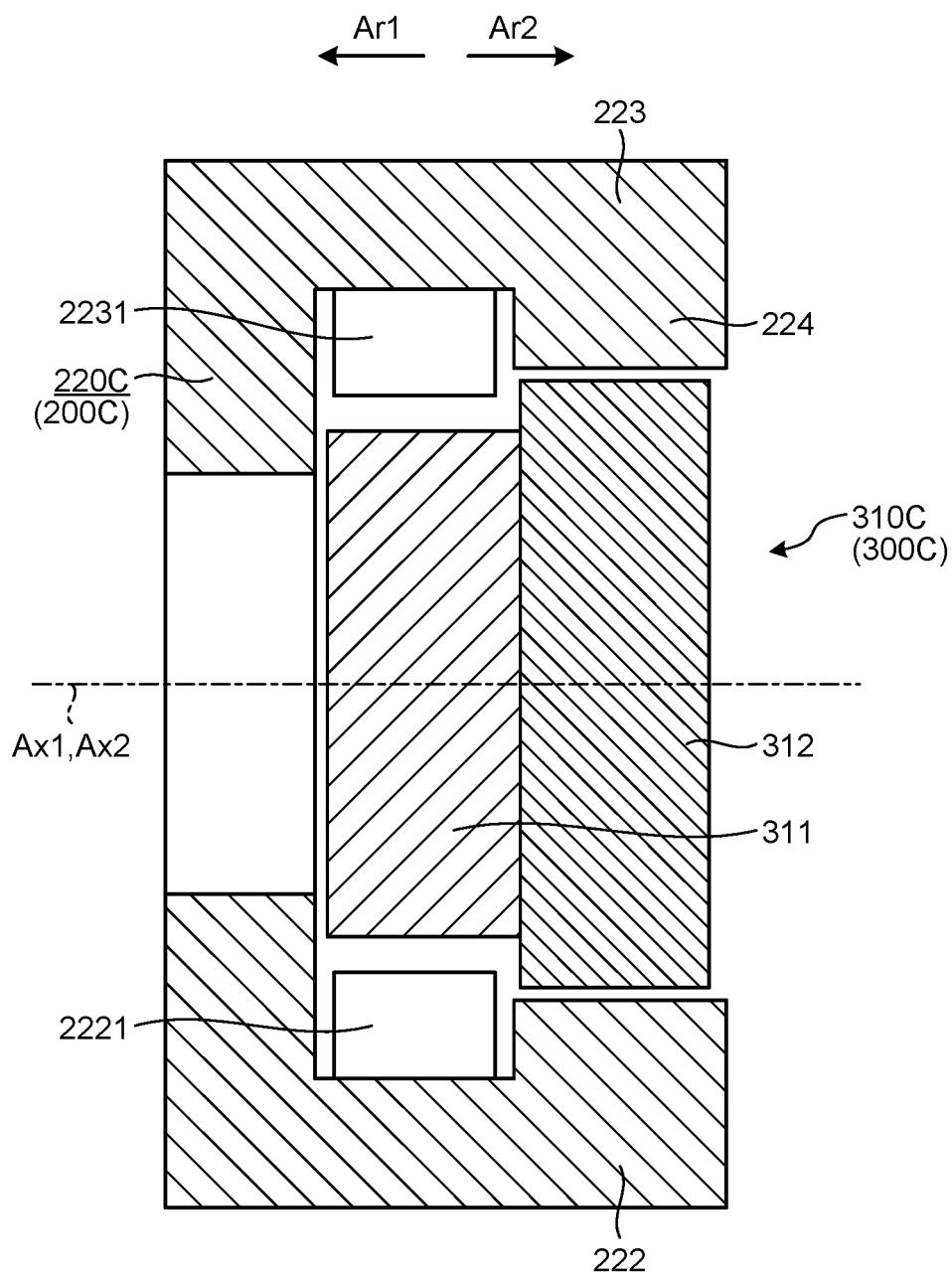
FIG. 17 is a diagram explaining a third modification of the embodiment.

FIG. 17 is a diagram explaining the third modification of the embodiment. Specifically, FIG. 17 is a cross-section cut along a plane along the center axis Ax1 in a state in which the torque wrench 200C is engaged with the rotary knob 300C.

In the rotary knob 300C according to the third embodiment, positions of the first and the second engaged portions 311, 312 are inverted from the rotary knob 300A explained in the first modification described above. That is, the first engaged portion 311 is positioned on the proximal end side Ar2 relative to the second engaged portion 312 as illustrated in FIG. 17.

Moreover, in the first engaged portion 311 according to the third modification, the groove portion 3111 explained in the first modification described above is omitted. That is, an outer diameter of the first engaged portion 311 is larger than an outer diameter of the second engaged portion 312.

Furthermore, in the torque wrench 200C according to the third embodiment, an inner peripheral surface of the head 220C has a shape described below.

When the head 220C is divided into two areas by a plane perpendicular to the center axis Ax2, one area in which the first and the second protrusion portions 2221, 2231 are arranged is positioned on the distal end side Ar1 relative to the other area 224 as illustrated in FIG. 17. Moreover, the inner diameter of the inner peripheral surface of the other area 224 is set to be a little larger than the outer diameter of the first engaged portion 311.

Also when the rotary knob 300C according to the third embodiment explained above is adopted, entrance of the end portion 2222 into the groove portion 3111 can be avoided, and misalignment of the center axes Ax1, Ax2 can be suppressed by the other area 224 at the operation of the torque wrench 200C. Therefore, an effect similar to that of the first modification described above is produced.

The first to the third modifications described above include the disclosure according to Notes 1 to 10 below.

1. An ultrasound treatment tool including:

a vibration generation source that includes a first screw, and that generates an ultrasound vibration;

a vibration transmitting member that is formed in an elongated shape, that has a blade at a distal end of the vibration transmitting member, and that has, at a proximal end of the vibration transmitting member, a second screw to be connected to the vibration generation source; and a rotary knob that is rotatable with the vibration transmitting member about a longitudinal axis of the vibration transmitting member, wherein the rotary knob includes a first engaged portion that is not engaged with a claw portion of a torque wrench; and a second engaged portion that engages with the claw portion of the torque wrench, and the first engaged portion suppresses misalignment of a rotation center axis of the rotary knob and a rotation center axis of the torque wrench by avoiding hooking on to the torque wrench when the torque wrench is rotated.

2. The ultrasound treatment tool according to Note 1, wherein

The first engaged portion is arranged on a distal end side relative to the second engaged portion, a groove portion into which the claw portion can be inserted is arranged in the first engaged portion, and a slanted surface is arranged on a side surface constituting the groove portion.

3. The ultrasound treatment tool according to Note 1, wherein in the second engaged portion, an engaging portion in which an outer diameter about the rotation center axis of the rotary knob increases along a rotation direction of the torque wrench, and the outer diameter becomes small at a predetermined rotation position is arranged.

4. The ultrasound treatment tool according to Note 3, wherein the slanted surface has a shape in which a diameter about the rotation center axis of the rotary knob gradually increases along the rotation direction of the torque wrench.

5. The ultrasound treatment tool according to Note 2, wherein the groove portion is arranged in plurality, and the slanted surface is arranged in all of a plurality of the groove portions.

6. The ultrasound treatment tool according to Note 1, wherein the first engaged portion is arranged on a distal end side relative to the second engaged portion, and an outer diameter of the first engaged portion is smaller than an outer diameter of the second engaged portion.

7. The ultrasound treatment tool according to Note 6, wherein the outer diameter of the first engaged portion is smaller than a distance between the claw portion and the rotation center axis of the torque wrench.

8. The ultrasound treatment tool according to Note 1, wherein the first engaged portion is arranged on a proximal end side relative to the second engaged portion.

9. The ultrasound treatment tool according to Note 8, wherein an outer diameter of the first engaged portion is equal to or larger than an outer diameter of the second engaged portion.

10. The ultrasound treatment tool according to Note 1, wherein the rotary knob further includes a rotation operating portion that receives a rotation operation that is a user operation.

Fourth Embodiment

As the jaw 12 according to the embodiment described above, a configuration according to a fourth modification described below may be adopted.

Hereinafter, for convenience of explanation, a treatment tool according to the fourth modification is denoted as treatment tool 2D. Moreover, a jaw according to the fourth modification is denoted as jaw 12D.

Figure 18:
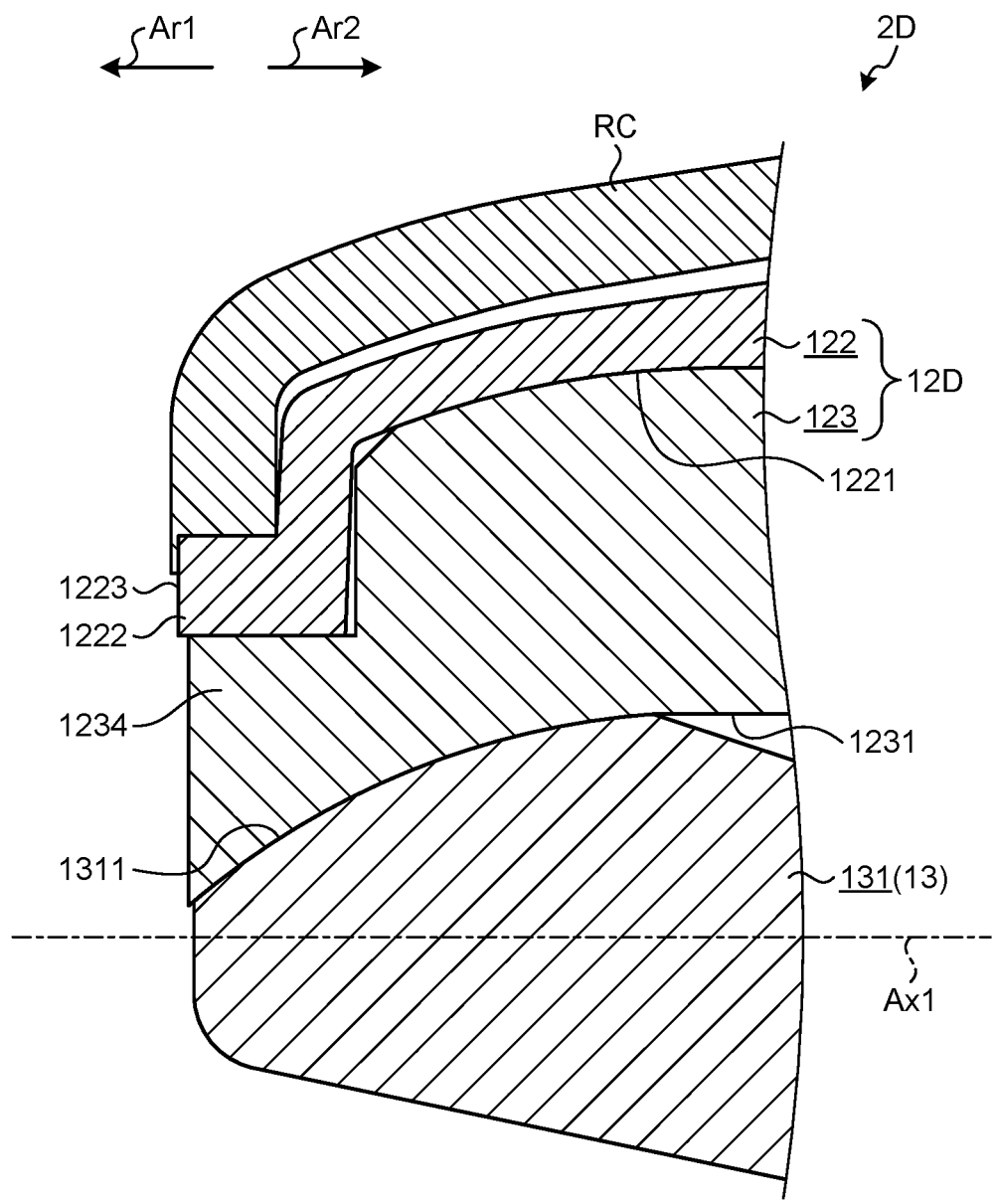
FIG. 18 is a diagram explaining a fourth modification of the embodiment.
Figure 19:
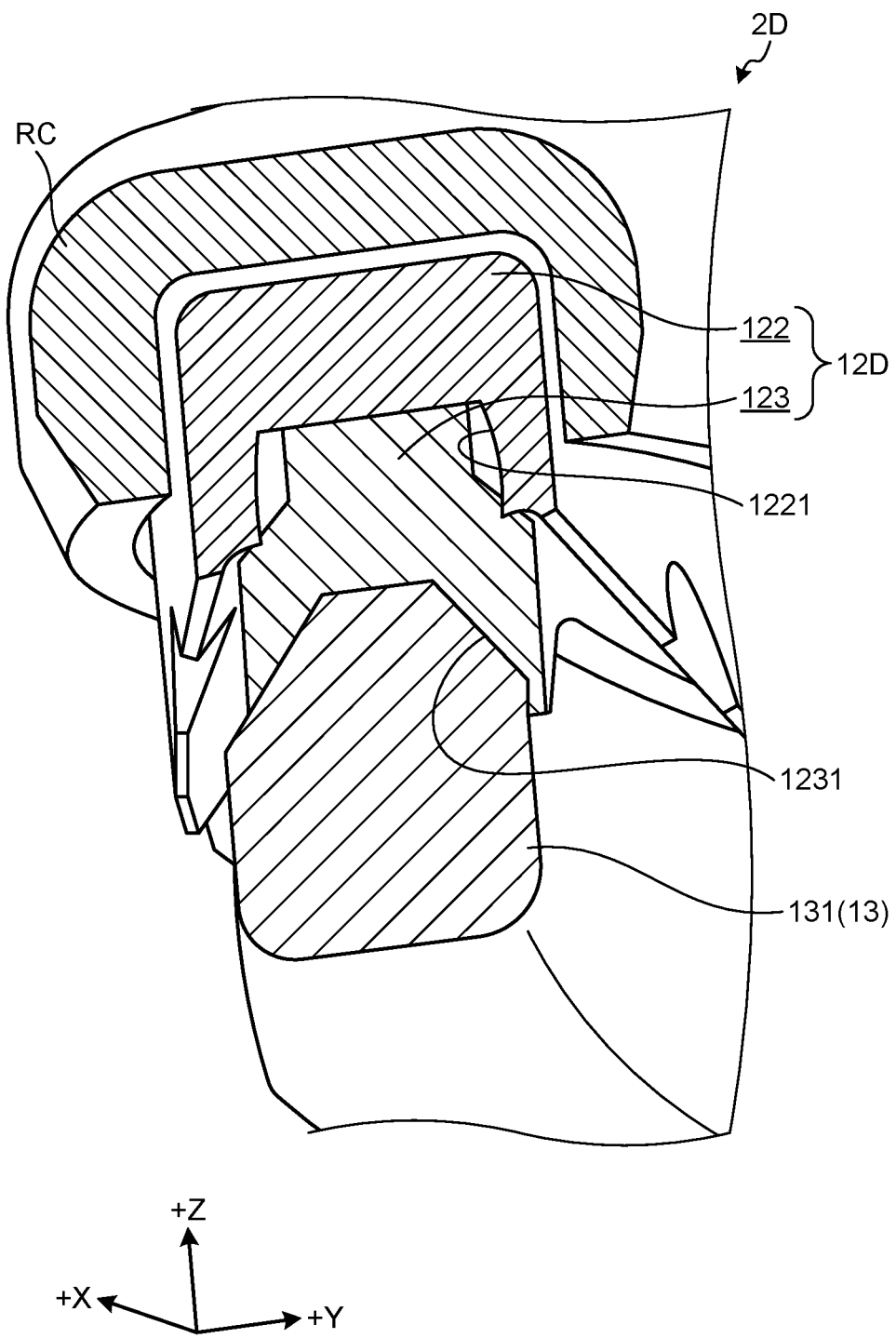
FIG. 19 is a diagram explaining the fourth modification of the embodiment.
Figure 20:
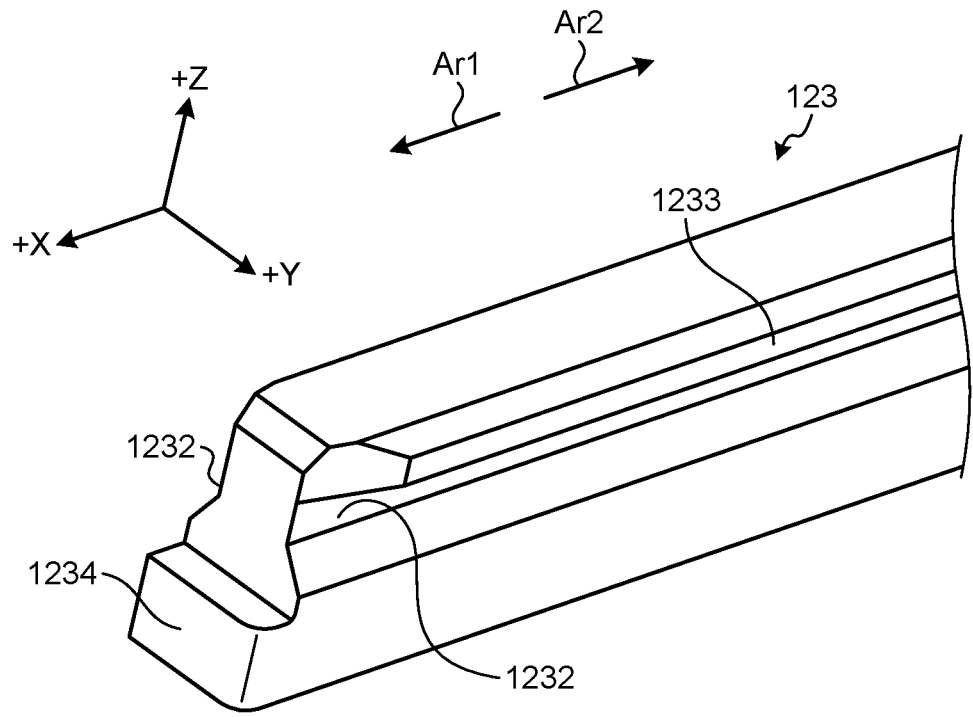
FIG. 20 is a diagram explaining the fourth modification of the embodiment.
Figure 21:
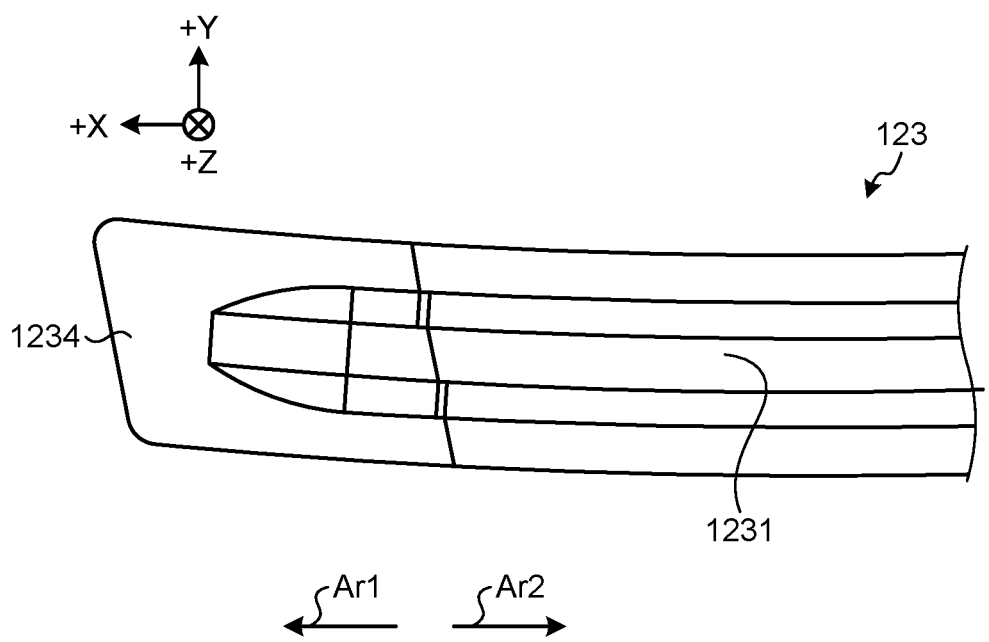
FIG. 21 is a diagram explaining the fourth modification of the embodiment.

FIG. 18 to FIG. 21 are diagrams explaining the fourth modification. Specifically, FIG. 18 is a cross-section of a distal end portion of the treatment tool 2D cut along an XZ plane including the center axis Ax1, and viewed from the +Y axis side. FIG. 19 is a cross-section of the distal end portion of the treatment tool 2D taken along a YZ plane, and viewed from a +X axis side. FIG. 18 and FIG. 19 illustrate a state in which the jaw 12D is brought close to the treating portion 131. FIG. 20 is a diagram of a distal end portion of a pad 123 viewed from the +X axis side. FIG. 21 is a diagram of the distal end portion of the pad 123 viewed from the −Z axis side.

The jaw 12D according to the fourth modification includes a pad holder 122 and the pad 123.

The pad holder 122 is an elongated-shaped member that is made from a metallic material. The pad holder 122 is axially supported in a rotatable manner about the second rotation axis Rx2 with respect to the first pin 101 on the proximal end side Ar2, and the second pin 121 is fixed thereto. That is, the jaw 12D opens and closes with respect to the treating portion 131 as the pad holder 122 rotates about the second rotation axis Rx2.

In this pad holder 122, on a surface on the −Z axis side, a concave portion 1221 that extends along a longitudinal direction of the pad holder 122 is arranged as illustrated in FIG. 18 and FIG. 19. In this concave portion 1221, a side wall on the proximal end side Ar2 is removed. That is, the concave portion 1221 communicates with an outside on the proximal end side Ar2.

Furthermore, in a distal end of the pad holder 122, at an end portion on the −Z axis side, a distal-end bending portion 1222 that protrudes toward the distal end side Ar1 parallel to the XY plane is arranged as illustrated in FIG. 18. An end surface on the −Z axis side in this distal-end bending portion 1222 is formed by a plane (plane parallel to the XY plane) extending an opening surface of the concave portion 1221. Moreover, a distal end surface 1223 (FIG. 18) of the distal-end bending portion 1222 is formed by a plane parallel to the YZ plane.

The distal-end bending portion 1222 is formed in a flat plate shape, cross-sectional areas of cross-sections cut along the YZ plane of which are substantially uniform from the proximal end side Ar2 to the distal end side Ar1 in FIG. 18, but it is not limited thereto. For example, arranging a slanted surface on an end surface on the −Z axis side of the distal-end bending portion 1222, it may have a shape in which the cross-sectional area of the cross section cut along the YZ plane of the distal-end bending portion 1222 becomes smaller as it approaches the distal end side Ar1.

In the pad holder 122 explained above, a cover RC made from resin having electrical insulation is arranged as illustrated in FIG. 18 and FIG. 19.

The cover RC is arranged so as to cover an outer surface excluding a surface on the −Z axis side of the pad holder 122 and the distal end surface 1223. The cover RC may be formed by insert molding with respect to the pad holder 122, or a structure of fixing to the pad holder 122 by a snap fit mechanism or a metallic pin may be adopted.

A first flat surface including the distal end surface 1223 and a second flat surface passing through a distal end of the cover RC and perpendicular to the center axis Ax1 are arranged to be substantially flush with each other. More specifically, the distal end of the cover RC is positioned within a range between a state of sticking out toward the distal end side Ar1 up to 0.5 mm and a state of retracting toward the proximal end side Ar2 up to 0.5 mm.

The pad 123 is softer than the vibration transmitting member 13, and is made from a resin material having an electrical insulating material and a biological compatibility, for example, polytetrafluoroethylene (PTFE). The pad 123 is supported with respect to the pad holder 122, and abuts on a slanted surface 1311 (FIG. 18) of the treating portion 131 when the jaw 12D is brought close to the treating portion 131. This slanted surface 1311 is a slanted surface with which a cross sectional area of a cross section cut along the YZ plane in the treating portion 131 decreases gradually toward the distal end side Ar1.

The pad 123 has a substantially rectangular parallelepiped shape extending substantially linearly as illustrated in FIG. 20 and FIG. 21.

In this pad 123, on a surface on the −Z axis side, a concave portion 1231 extending along the longitudinal direction of the pad 123 is arranged as illustrated in FIG. 18, FIG. 19, and FIG. 21. In this concave portion 1231, a side wall on the proximal end side Ar2 is removed. That is, the concave portion 1231 communicates with an outside on the proximal end side Ar2.

Moreover, in the pad 123, on each side surface perpendicular to the Y axis, a slit 1232 passing through from the distal end to the proximal end is arranged as illustrated in FIG. 20. Hereinafter, for convenience of explanation, out of the respective side surfaces perpendicular to the Y axis in the pad 123, a protruding portion on the +Z axis side relative to the slit 1232 is denoted as engaging portion 1233 (FIG. 20).

The pad 123 is supported with respect to the pad holder 122 as the portion on the −Z axis side is inserted into the inside of the concave portion 1221, and a pair of the engaging portions 1233 are engaged on an inner side surface of the concave portion 1221.

Moreover, at the distal end of the pad 123, a protruding portion 1234 that protrudes parallel to the XY plane toward the distal end side Ar1 is arranged at an end portion on the −Z axis side as illustrated in FIG. 18 and FIG. 20. This protruding portion 1234 is positioned on the −Z axis side of the distal-end bending portion 1222 in a state in which the pad 123 is supported with respect to the pad holder 122. Furthermore, an end surface on the +Z axis side in the protruding portion 1234 is constituted of a plane parallel to the XY plane. That is, the end surface on the +Z axis side in the protruding portion 1234 is to be parallel to the end surface on the −Z axis side in the distal-end bending portion 1222. In a state in which the jaw 12D is brought close to the treating portion 131 and the pad 123 abuts on the slanted surface 1311 of the treating portion 131, the end surface on the +Z axis side in the protruding portion 1234 abuts on the end surface on the −Z axis side in the distal-end bending portion 1222.

A first plane including the distal end surface 1223 and a third plane passing through a distal end of the protruding portion 1234, and perpendicular to the center axis Ax1 are arranged to be substantially flush with each other. More specifically, the distal end of the protruding portion 1234 is positioned within a range between a state of sticking out from the distal end surface 1223 toward the distal end side Ar1 up to 0.5 mm and a state of retracting toward the proximal end side Ar2 up to 0.5 mm.

The first plane including the distal end surface 1223 and a fourth plane perpendicular to the center axis Ax1 are also arranged to be substantially flush with each other. More specifically, the distal end of the treating portion 131 is positioned within a range between a state of sticking out from the distal end surface 1223 toward the distal end side Ar1 up to 0.5 mm and a state of retracting toward the proximal end side Ar2 up to 0.5 mm.

In the fourth modification, as illustrated in FIG. 18, the first plane including the distal end surface 1223 and a second plane passing through the distal end of the cover RC and perpendicular to the center axis Ax1, and the third plane passing through the distal end of the protruding portion 1234 and perpendicular to the center axis Ax1, and the fourth plane passing through the distal end of the treating portion 131 and perpendicular to the center axis Ax1 are arranged to be substantially flush with one another, but it is not limited thereto. As long as the treating portion 131 and the pad holder 122 do not contact with each other, the distal end of the treating portion 131 may be positioned on the distal end side Ar1 relative to the distal end surface 1223, or the distal end of the protruding portion 1234 may be positioned on the proximal end side Ar2 relative to the distal end surface 1223.

In the fourth modification, for example, when a high frequency energy is applied to a target site, the control device 3 supplies a high frequency power to a portion between the pad holder 122 and the vibration transmitting member 13 through the electrical cable C. When a high frequency power is supplied to the portion between the pad holder 122 and the vibration transmitting member 13, the high frequency current flows through the target portion grasped between the pad holder 122 and the treating portion 131. That is, the pad holder 122 and the treating portion 131 respectively function as electrodes.

According to the fourth modification explained above, a following effect is produced.

When the cover RC is provided, the distal end of the cover RC tends to be positioned at a position protruding from the distal end of the pad 123 toward the distal end side Ar1. In this state, a performance of grasping a living tissue at the distal end is degraded as the distal end of the cover RC protrudes toward the distal end side Ar1 relative to the distal end of the pad 123.

In the treatment tool 2D according to the fourth modification, the first plane including the distal end surface 1223, the second plane passing through the distal end of the cover RC and perpendicular to the center axis Ax1, the third plane passing through the distal end of the protruding portion 1234 and perpendicular to the center axis Ax1, and the fourth plane passing through the distal end of the treating portion 131 and perpendicular to the center axis Ax1 are arranged to be substantially flush with one another. Therefore, even when the cover RC is arranged, the performance of grasping a living tissue at the distal end is not to be degraded.

Particularly, in a state in which the jaw 12D is brought close to the treating portion 131, and the pad 123 abuts on the slanted surface 1311 of the treating portion 131, the end surface of the protruding portion 1234 on the +Z axis side abuts on the end surface of the distal-end bending portion 1222 on the −Z axis side. Accordingly, even when a living tissue is grasped at the distal end, the living tissue can be grasped with a relatively high grasping power with the protruding portion 1234 and the treating portion 131.

Moreover, in the treatment tool 2D according to the fourth modification, the protruding portion 1234 is positioned between the treating portion 131 and the distal-end bending portion 1222. Therefore, a structure in which the treating portion 131 and the distal-end bending portion 1222 do not contact each other can be implemented.

Moreover, in the treatment instrument 2D according to the fourth modification, the distal-end bending portion 1222 is positioned between the distal end of the cover RC and the protruding portion 1234. Therefore, the cover RC and the pad 123 are not allowed to contact each other, and heat from the pad 123 is not to be transmitted to the cover RC. That is, it is possible to prevent the cover RC from being melted by the heat.

In the fourth modification described above, the pad holder 122 is axially supported with respect to the first pin 101 in a rotatable manner about the second rotation axis Rx2 on the proximal end side Ar2, and the second pin 121 is fixed thereto, but it is not limited thereto, and a following configuration may be adopted.

For example, as the jaw 12D, a jaw main body is provided besides the pad holder 122 and the pad 123. The jaw main body is axially supported with respect to the first pin 101 in a rotatable manner about the second rotation axis Rx 2 on the proximal end side Ar2, and the second pin is fixed thereto. The pad holder 122 is supported with respect to the jaw main body in a swingable manner about a rotation axis substantially parallel to the second rotation axis Rx2.

The fourth modification described above includes the disclosure according to Notes 11 to 19 below.

11. An ultrasound treatment tool including:
a vibration transmitting member that is formed in an elongated shape, and that transmits an ultrasound vibration generated by a vibration generation source to a distal end portion of the vibration transmitting member;
a treating portion that is arranged at the distal end portion of the vibration transmitting member, and that has a slanted surface; and
a jaw that opens and closes with respect to the treating portion, wherein
the jaw includes:
a pad made from resin that abuts on the slanted surface in a state in which the jaw is closed with respect to the treating portion;
a pad holder made from metal that holds the pad; and
a cover made from resin that covers at least a part of an outer surface of the pad holder, wherein
a protruding portion that protrudes toward a side of the distal end side is arranged in the pad,
a distal-end bending portion that protrudes toward the side of the distal end is arranged in the pad holder, and
the protruding portion and the distal-end bending portion abut on each other in the state in which the jaw is closed with respect to the treating portion.

12. The ultrasound treatment tool according to Note 11, wherein
a first plane that passes through a distal end of the distal-end bending portion, and that is perpendicular to a center axis along a longitudinal direction of the vibration transmitting member and a second plane that passes through a distal end of the cover, and that is perpendicular to the center axis are substantially flush with each other.

13. The ultrasound treatment tool according to Note 12, wherein
a distance between the first plane and the second plane is equal to or larger than 0 mm, and equal to or smaller than 0.5 mm.

14. The ultrasound treatment tool according to Note 11, wherein
a first plane that passes through a distal end of the distal-end bending portion, and that is perpendicular to a center axis along a longitudinal direction of the vibration transmitting member and a third plane that passes through a distal end of the protruding portion, and that is perpendicular to the center axis are substantially flush with each other.

15. The ultrasound treatment tool according to Note 14, wherein
a distance between the first plane and the third plane is equal to or larger than 0 mm, and equal to or smaller than 0.5 mm.

16. The ultrasound treatment tool according to Note 11, wherein
a first plane that passes through a distal end of the distal-end bending portion, and that is perpendicular to a center axis along a longitudinal direction of the vibration transmitting member and a fourth plane that passes through a distal end of the treating portion, and that is perpendicular to the center axis are substantially flush with each other.

17. The ultrasound treatment tool according to Note 16, wherein
a distance between the first plane and the fourth plane is equal to or larger than 0 mm, and equal to or smaller than 0.5 mm.

18. The ultrasound treatment tool according to Note 11, wherein
end surfaces of the distal-end bending portion and the protruding portion that face each other are parallel to each other.

19. The ultrasound treatment tool according to Note 11, further including
a shaft into which the vibration transmitting member is inserted, wherein
the pad holder is axially supported in a rotatable manner with respect to the shaft, and
the jaw opens and closes with respect to the treating portion as the pad holder rotates with respect to the shaft.

REFERENCE SIGNS LIST

1 TREATMENT SYSTEM
2, 2D ULTRASOUND TREATMENT TOOL
3 CONTROL DEVICE
4 HANDPIECE
5 ULTRASOUND TRANSDUCER
6 FIXED HANDLE
7 MOVABLE HANDLE
8 SWITCH
9 ROTARY KNOB
10 SHAFT
11 OPENING CLOSING MECHANISM
12, 12D JAW
13 VIBRATION TRANSMITTING MEMBER
51 TD CASE
52 ULTRASOUND TRANSDUCER
61 CASING BODY
62 HANDLE MAIN BODY
71 HANDLE BASE PORTION
72 OPERATING PORTION
73 CONNECTING PORTION
91 CONNECTING SURFACE
92 PIN
94 CONCAVE PORTION
101 FIRST PIN
102 NOTCH PORTION
111 INNER PIPE
112 HOLDER
113 SLIDER REST
114 SLIDER
115 COIL SPRING
121 SECOND PIN
122 PAD HOLDER
123 PAD
131 TREATING PORTION
132 INTERNAL THREAD
200, 200B, 200C TORQUE WRENCH
210 ARM
220, 220B, 220C HEAD
221 SLIT
222 FIRST ENGAGEMENT ARM
223 SECOND ENGAGEMENT ARM
224 OTHER AREA
300, 300A TO 300C ROTARY KNOB
310, 310A TO 310C ENGAGED PORTION
311 FIRST ENGAGED PORTION
312 SECOND ENGAGED PORTION
320 ROTATION OPERATING PORTION
521 EXTERNAL THREAD
611 FIRST PROTRUSION PORTION
612 SECOND PROTRUSION PORTION
613 HOUSING PORTION
911 PROTRUDING PORTION
912 PRESS FITTING HOLE
913 SECOND THROUGH HOLE
931 FIRST PROTRUDING PORTION
932 SECOND PROTRUDING PORTION
1111 ARM PORTION
1121 NOTCH PORTION
1122 ARC PORTION
1123 PROTRUSION PORTION
1124 FIRST THROUGH HOLE
1125 FLANGE
1131 CONNECTION BASE
1132 INSERTION HOLE
1133 HOLE
1134 INSERTION PORTION
1221 CONCAVE PORTION
1222 DISTAL-END BENDING PORTION
1223 DISTAL END SURFACE
1231 CONCAVE PORTION
1232 SLIT
1233 ENGAGING PORTION
1234 PROTRUDING PORTION
1311 SLANTED SURFACE
2221 FIRST PROTRUSION PORTION
2222 END PORTION
2231 SECOND PROTRUDING PORTION
2232 END PORTION
3111 GROOVE PORTION
3112 SLANTED SURFACE
3121 ENGAGING PORTION
Ar1 DISTAL END SIDE
Ar2 PROXIMAL END SIDE
Ax1, Ax2 CENTER AXIS
C ELECTRICAL CABLE
P1 ELECTRICALLY COMMUNICATION PATH
RC COVER
Rx1 FIRST ROTATION AXIS
Rx2 SECOND ROTATION AXIS
TI INNER TUBE
TO OUTER TUBE

What is claimed is:
1. An ultrasound treatment tool, comprising:
a handle;
a vibration transmitting member configured to transmit an ultrasonic vibration;
a holder located about an outer circumference surface of the vibration transmitting member;
a rotary knob configured to rotate about a longitudinal axis of the vibration transmitting member in response to a user operation; and
a slider provided on the holder and configured to move along the longitudinal axis between a first position and a second position,
wherein the holder and the rotary knob are integrally coupled with each other,
wherein, in the first position, a proximal portion of the slider and a distal portion of the slider are both located in the handle,
wherein an inner surface of the handle includes a proximal protrusion portion that protrudes in a radially inward direction relative to the longitudinal axis,
wherein the holder includes a flange protruding in a radially outward direction relative to the longitudinal axis,
wherein the flange is positioned in the proximal protrusion portion, and
wherein the flange and the proximal protrusion portion are disposed proximally relative to the slider.
2. The ultrasound treatment tool according to claim 1, wherein the holder and the rotary knob are integrally coupled by a press-fitting.

3. The ultrasound treatment tool according to claim 2, wherein the holder includes a distal protrusion portion located at a distal end of the holder.

4. The ultrasound treatment tool according to claim 3, wherein the distal protrusion portion includes one or more pairs of protrusions that project radially inward from an inner peripheral surface.

5. The ultrasound treatment tool according to claim 1, further comprising a pin passing through the holder and the rotary knob that extends along a direction intersecting the longitudinal axis,
wherein the pin maintains a relative positional relationship between the holder and the rotary knob along the longitudinal axis.

6. The ultrasound treatment tool according to claim 1, further comprising a slider rest on which the slider is slidably disposed,
wherein the slider rest is in contact with the rotary knob, and
wherein the slider rest is configured to rotate with the rotary knob when the rotary knob is rotated by the user operation.

7. The ultrasound treatment tool according to claim 6, wherein the proximal protrusion portion is located proximally relative to the slider rest.

8. The ultrasound treatment tool according to claim 1, further comprising:
a cylindrical pipe into which the vibration transmitting member is inserted; and
a jaw disposed at a distal end of the cylindrical pipe, wherein at least a part of the cylindrical pipe is formed of a first conductive material,
wherein at least a part of the jaw is formed of a second conductive material, and
wherein the jaw and a distal end of the vibration transmitting member are configured to grasp a tissue between the jaw and the distal end of the vibration transmitting member.

9. The ultrasound treatment tool according to claim 8, wherein the holder is formed of an electrically insulating material and includes an electrical communication path to flow a high-frequency current, and
wherein the electrical communication path electrically connects the jaw to the cylindrical pipe.

10. The ultrasound treatment tool according to claim 1, wherein the proximal protrusion portion comprises a pair of protrusion segments, and
wherein the flange is sandwiched between the pair of protrusion segments.

11. The ultrasound treatment tool according to claim 1, wherein the proximal protrusion portion has a ring-shape,
wherein the proximal protrusion includes a slot that recesses in a direction away from the longitudinal axis and extends in a circumferential direction about the longitudinal axis.

12. An ultrasound treatment system comprising:
the ultrasound treatment tool according to claim 1; and
a control device configured to control the ultrasonic vibration.

13. The ultrasound treatment tool according to claim 1, wherein a location of at least one of the holder and the rotary knob is fixed relative to the handle along the longitudinal axis.

14. The ultrasound treatment tool according to claim 1, wherein both the holder and the rotary knob are positioned radially relative to the longitudinal axis.

15. The ultrasound treatment tool according to claim 1, wherein the proximal protrusion portion comprises a first proximal protrusion and a second proximal protrusion,
wherein, in the radially inward direction, the first proximal protrusion is longer than the second proximal protrusion, and
wherein an inner surface of the first proximal protrusion is in contact with the holder in a different position from the flange.

16. The ultrasound treatment tool according to claim 1, wherein the inner surface of the handle further includes a ring-shaped protrusion portion disposed distally relative to the proximal protrusion portion,
wherein the rotary knob comprises a concave portion, and
wherein the ring-shaped protrusion portion is located in the concave portion.

17. The ultrasound treatment tool according to claim 1, wherein the first position is on a proximal side of a position at which the holder and the rotary knob are coupled.

18. The ultrasound treatment tool according to claim 1, wherein the first position is proximal relative to the second position.

19. The ultrasound treatment tool according to claim 1, wherein, in the second position, the distal portion of the slider is located in the rotary knob.

20. The ultrasound treatment tool according to claim 1, wherein the first position is proximal relative to the second position, and
wherein, in the second position, the distal portion of the slider is located in the rotary knob.

* * * * *